(12) United States Patent
He et al.

(10) Patent No.: US 11,414,437 B2
(45) Date of Patent: Aug. 16, 2022

(54) BORATE COMPOUND, AND SYNTHESIS METHOD THEREFOR AND USES THEREOF

(71) Applicant: CHENGDU ORIGIN BIOTECHNOLOGY LIMITED COMPANY, Sichuan (CN)

(72) Inventors: Peng He, Sichuan (CN); Xuechao Wang, Sichuan (CN); Ta Deng, Sichuan (CN); Hai Zhao, Sichuan (CN); Shuang Chen, Sichuan (CN); Haiyan Li, Sichuan (CN); Guangxin Dong, Sichuan (CN)

(73) Assignee: CHENGDU ORIGIN BIOTECHNOLOGY LIMITED COMPANY, Sichuan (CN)

( * ) Notice: Subject to any disclaimer, the term of this patent is extended or adjusted under 35 U.S.C. 154(b) by 133 days.

(21) Appl. No.: 16/632,637

(22) PCT Filed: Jul. 27, 2018

(86) PCT No.: PCT/CN2018/097360
§ 371 (c)(1),
(2) Date: Jan. 21, 2020

(87) PCT Pub. No.: WO2019/020099
PCT Pub. Date: Jan. 31, 2019

(65) Prior Publication Data
US 2020/0165272 A1    May 28, 2020

(30) Foreign Application Priority Data
Jul. 28, 2017 (CN) .......................... 201710630397.6

(51) Int. Cl.
*C07F 5/04* (2006.01)
*A61P 35/00* (2006.01)

(52) U.S. Cl.
CPC ............... *C07F 5/04* (2013.01); *A61P 35/00* (2018.01)

(58) Field of Classification Search
CPC ........................................................ C07F 5/04
See application file for complete search history.

(56) References Cited

U.S. PATENT DOCUMENTS

| | | | |
|---|---|---|---|
| 9,175,018 B2 | 11/2015 | Elliott et al. | |
| 9,862,745 B2 | 1/2018 | Ammoscato et al. | |
| 2016/0368945 A1 | 12/2016 | Han | |
| 2021/0332069 A1* | 10/2021 | He | ............... C07F 5/025 |

FOREIGN PATENT DOCUMENTS

| | | | |
|---|---|---|---|
| CN | 101772507 A | 7/2010 | |
| CN | 102066386 A | 5/2011 | |
| CN | 103204867 A | 7/2013 | |
| CN | 103435638 A | 12/2013 | |
| CN | 1960996 B | 4/2016 | |
| CN | 106608883 A | 5/2017 | |
| CN | 106659761 A | 5/2017 | |
| CN | 106916177 A | 7/2017 | |
| CN | 107400142 A | 11/2017 | |
| WO | 2009020448 A1 | 2/2009 | |
| WO | 2009154737 A1 | 12/2009 | |
| WO | WO-2009154737 A1 * | 12/2009 | ............. A61P 31/18 |
| WO | 2012177835 A1 | 12/2012 | |
| WO | 2016205790 A2 | 12/2016 | |

OTHER PUBLICATIONS

English translation of International Search Report for International Application No. PCT/CN2018/097360, dated Oct. 15, 2018, 6 pages.
CN Office Action for Patent Application CN 201810843619.7 dated Jun. 18, 2021; 12 pp.

* cited by examiner

*Primary Examiner* — John S Kenyon
(74) *Attorney, Agent, or Firm* — Armstrong Teasdale LLP

(57) ABSTRACT

A borate compound serving as a proteasome inhibitor, a preparation method for the borate compound and uses thereof.

16 Claims, 2 Drawing Sheets

BORATE COMPOUND, AND SYNTHESIS METHOD THEREFOR AND USES THEREOF

CROSS-REFERENCE TO RELATED APPLICATIONS

This application is a U.S. National Phase Application of PCT/CN2018/097360, filed Jul. 27, 2018, which claims the benefit of priority to CN Application No. 201710630397.6, filed Jul. 28, 2017, the contents of which are hereby expressly incorporated by reference in their entirety.

FIELD OF THE INVENTION

The present invention relates to the field of chemical medicines, and more particularly, to borate compounds serving as proteasome inhibitors. Another aspect of the present invention relates to synthesis methods for the compounds and use of the compounds in preparing medicaments for treating cancers.

BACKGROUND OF THE INVENTION

Boric acid and borate compounds show various biological activities applicable to medicines due to their unique structural characteristics. Proteasome is an important component of a ubiquitin-proteasome system, which is responsible for regulation and degradation of most intracellular proteins, and plays a central role in the regulation of cell cycle, cell proliferation and cell apoptosis. Bortezomib (trade name: Velcade®)), a boric acid medicine, was the first listed targeted proteasome inhibitor approved by FDA in 2003, which was a new anti-tumor medicine developed by Millennium Pharmaceutical Company in the United States, freeze-dried powder for injection, and for treating relapsed and refractory multiple myeloma. The Bortezomib can be selectively combined with threonine at an active site of the proteasome, and can be degraded and change a regulatory protein level in a body, destroy the stability of cells, and lead to the death of tumor cells.

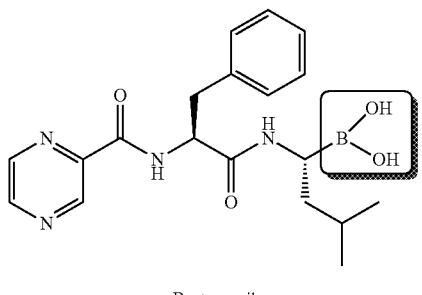

Bortezomib

Ixazomib Citrate (MLN9708, trade name: Ninlaro®) was the second-generation proteasome inhibitor developed by Millennium Pharmaceutical Company based on the Bortezomib. The Ixazomib Citrate was approved and listed by FDA on Nov. 20, 2015 for the treatment of Multiple Myeloma (MM). The Ixazomib Citrate can inhibit and be bound preferentially to a chymotrypsin-like proteolysis (β5) site of 20S proteasome, and inhibit proliferation of multiple myeloma cells by blocking the protease. A borate compound MLN9708, as a prodrug, is rapidly hydrolyzed into an active boric acid structure MLN2238 in vivo to exert a pharmacological activity. Due to the conversion of an unstable boric acid group into a stable borate structure, the MLN9708 has the greatest advantage in changing an injection form into an oral capsule form compared with the MLN2238 and the Bortezomib, which greatly improves the drug compliance of patients.

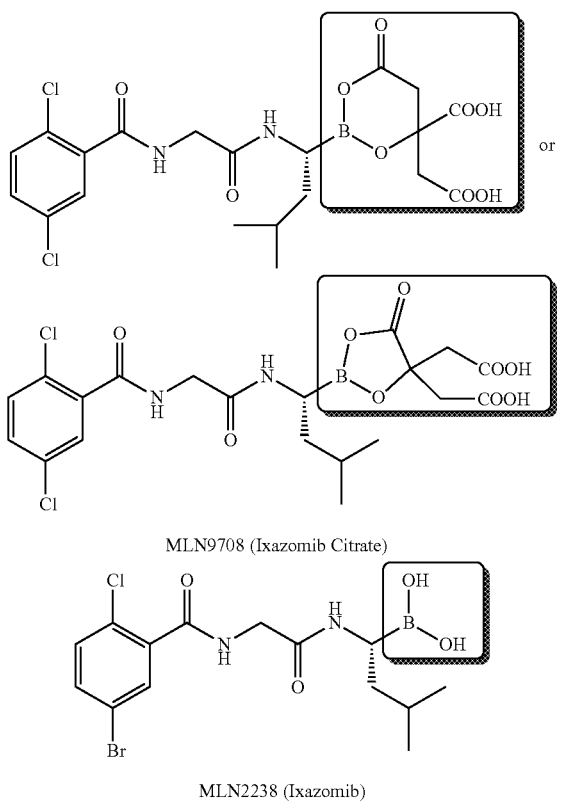

MLN9708 (Ixazomib Citrate)

MLN2238 (Ixazomib)

According to present patent documents WO2009154737, CN102066386A, CN103435638A, etc., the MLN9708 is obtained by synthesis via a one-step reaction of the MLN2238 with citric acid. Since the citric acid has the characteristics of both α-hydroxycarboxylic acid and β-hydroxycarboxylic acid, the citric acid has multiple sites that can react with the boric acid, resulting in two possibilities of a six-membered cyclic borate structure and a five-membered cyclic borate structure in the MLN9708, which brings a great difficulty to refining and purification of the MLN9708, and greatly increases production costs.

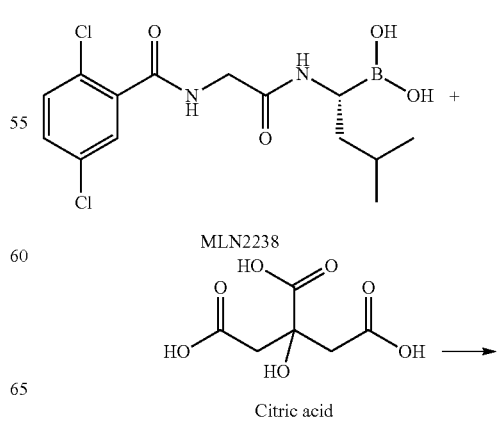

-continued

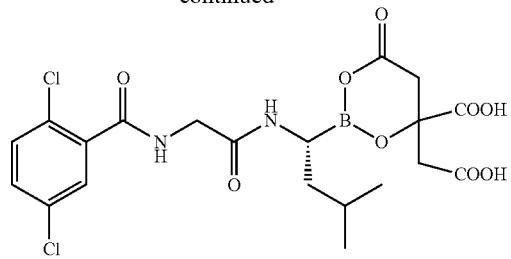

or

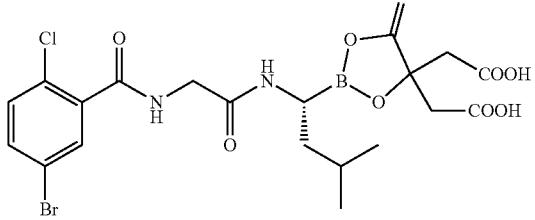

MLN9708

In addition, patent document CN103435638A discloses a compound (81) with a following structure in the embodiments thereof.

81

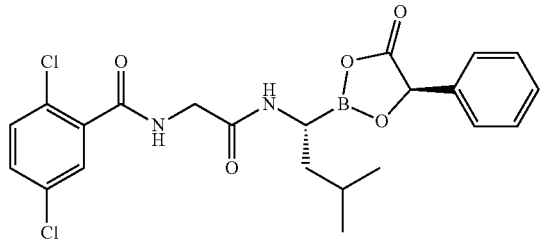

In the prior art, there is still a need to obtain a new borate compound which is easier to be refined and purified, and has higher biological activity and safety for treating a cancer.

SUMMARY OF THE INVENTION

In order to solve the technical problems above, the present invention provides a borate compound of formula I or a pharmaceutically acceptable salt thereof:

I

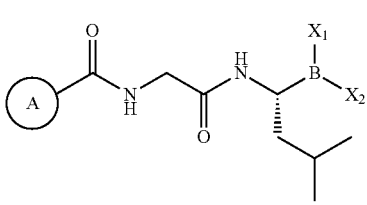

wherein $X_1$ and $X_2$ jointly form a circular portion derived from a boric acid esterifying agent by removing hydrogen atoms of two functional groups of said boric acid esterifying agent, and the circular portion is an optionally substituted ring in which a boron atom is directly linked to two oxygen atoms and formed jointly with other fragments; the boric acid esterifying agent is selected from the group consisting of α-hydroxy acid, β-hydroxy acid, amino acid and $R_3$—NH—$R_4$, the $R_3$ and the $R_4$ are independently selected from —$(CH_2)_n$COOH, and n=0, 1, 2, 3, 4 or 5; and ring A is selected from the group consisting of:

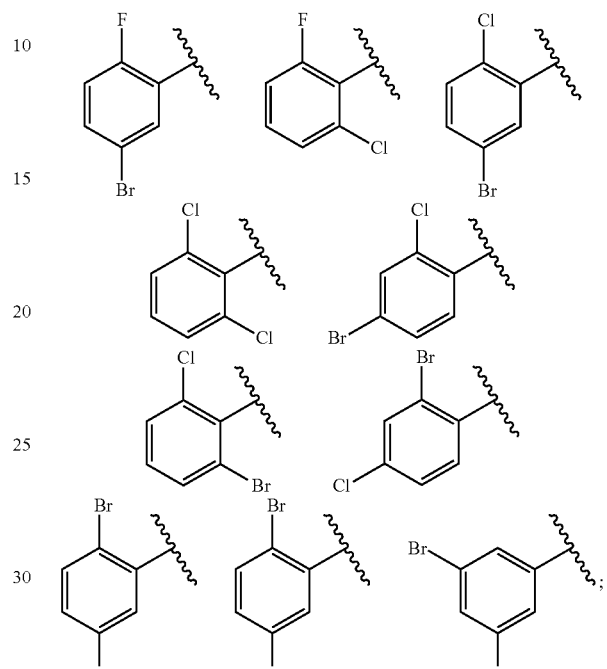

wherein, when the ring A is selected from the group consisting of

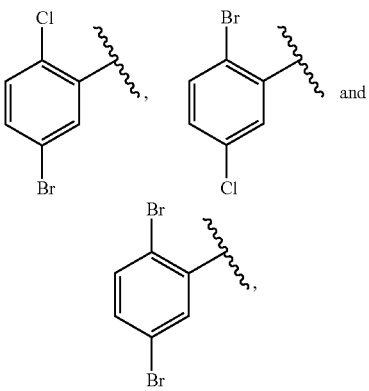

the α-hydroxy acid and the β-hydroxy acid do not include citric acid, malic acid and tartaric acid.

When the boric acid esterifying agent is $R_3$—NH—$R_4$, the boric acid esterifying agent can be iminodiformic acid, iminodiacetic acid, iminodipropionic acid, N-carboxyl-2-amine acetate or N-acetic acid-3-amine propionate, etc. Therefore, the $R_3$ and the $R_4$ can be the same or different.

Preferably, the $X_1$ and the $X_2$ jointly form the circular portion formed by removing the hydrogen atoms through the two functional groups of the boric acid esterifying agent, which is a 5 to 12 membered ring. For example, the circular portion may be a 5 membered ring, a 6 membered ring, a 7 membered ring, an 8 membered ring, a 9 membered ring, a 10 membered ring, an 11 membered ring and a 12 membered ring.

Preferably, the boric acid esterifying agent is selected from the group consisting of salicylic acid, mandelic acid, lactic acid and iminodiacetic acid substituted by a substituent or unsubstituted; the substituent is selected from the group consisting of halogens, amino, C1-6 alkyls, C3-C8 cycloalkyls, C2-C6 carboxyalkyls and C1-6 hydroxyalkyls and a mixture thereof; and optionally, phenyl in the salicylic acid or the mandelic acid substituted or unsubstituted by a substituent as the boric acid esterifying agent is hydrogenated or partially hydrogenated.

The mandelic acid is preferably R-mandelic acid or S-mandelic acid, and can also be racemic DL-mandelic acid; and the lactic acid is preferably L-lactic acid.

Preferably, when the ring A is

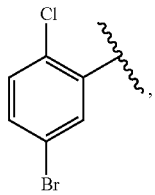 [SMILES: *c1cc(Br)ccc1Cl]

the boric acid esterifying agent is the salicylic acid, the mandelic acid or the lactic acid substituted or unsubstituted by a substituent, and is preferably a salicylic acid or a R-mandelic acid; and the substituent is selected from the group consisting of halogens, amino, C1-6 alkyls, C2-C6 carboxyalkyls and C1-6 hydroxyalkyls and a mixture thereof.

Preferably, when the ring A is selected from the group consisting of

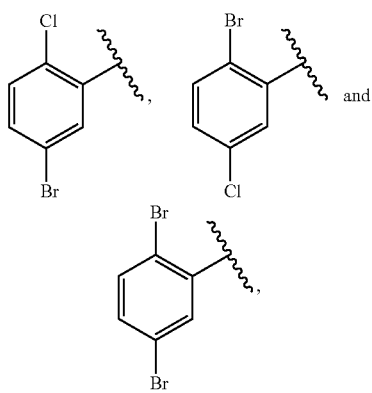

the boric acid esterifying agent is a salicylic acid, a R-mandelic acid or an L-lactic acid substituted or unsubstituted by a substituent; and the substituent is selected from the group consisting of halogens, amino, C1-6 alkyls, C2-C6 carboxyalkyls and C1-6 hydroxyalkyls and a mixture thereof; and optionally, the phenyl in the salicylic acid or the R-mandelic acid substituted or unsubstituted by a substituent as the boric acid esterifying agent is hydrogenated or partially hydrogenated.

Preferably, the compound of the present invention is selected from the group consisting of:

compound 8a:

2-chloro-5-bromo-N-(2-{[R)-3-methyl-1-(4-oxo-4H-1,3,2-benzodioxaborolan-2-yl)butyl]amino}-2-oxoethyl)benzamide

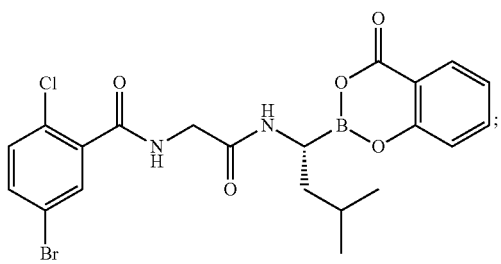

compound 8b:

2-chloro-5-bromo-N-[2-({(1R)-3-methyl-1-[(5R)-4-oxo-5-phenyl-1,3,2-dioxaborolan-2-yl]butyl}amino)-2-oxoethyl]benzamide

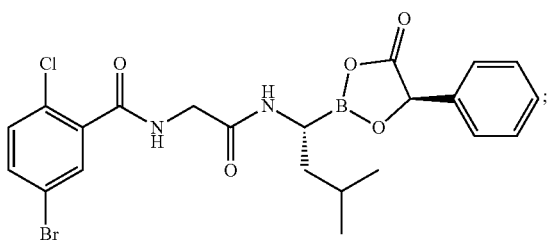

compound 8c:

2-chloro-5-bromo-N-[2-({(1R)-3-methyl-1-[(4S)-4-methyl-5-oxo-1,3,2-dioxaborolan-2-yl]butyl}amino)-2-oxoethyl]benzamide

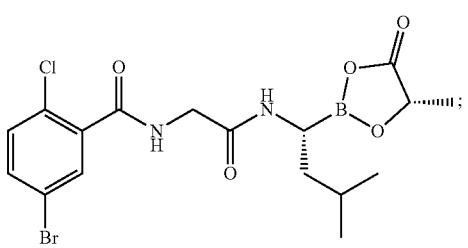

compound 8e:

2-bromo-5-bromo-N-(2-{[(1R)-3-methyl-1-(4-oxo-4H-1,3,2-benzodioxaborolan-2-yl)butyl]amino}-2-oxoethyl)benzamide

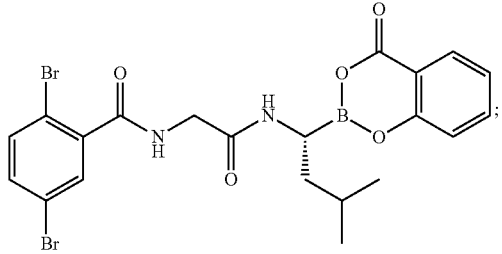

compound 8f:
2-bromo-5-bromo-N-[2-({(1R)-3-methyl-1-[(5R)-4-oxo-5-phenyl-1,3,2-dioxaborolan-2-yl]butyl}amino)-2-oxoethyl]benzamide

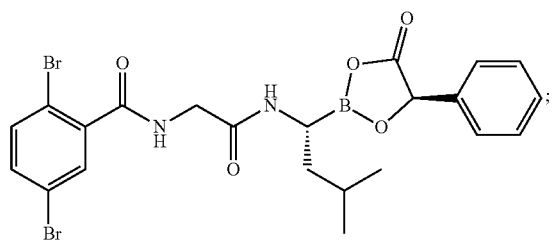

compound 8g:
2-bromo-5-bromo-N-[2-({(1R)-3-methyl-1-[(4S)-4-methyl-5-oxo-1,3,2-dioxaborolan-2-yl]butyl}amino)-2-oxoethyl]benzamide

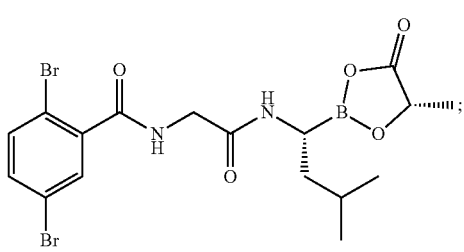

compound 8h:
2-bromo-5-chloro-N-(2-{[(1R)-3-methyl-1-(4-oxo-4H-1,3,2-benzodioxaborolan-2-yl)butyl]amino}-2-oxoethyl)benzamide

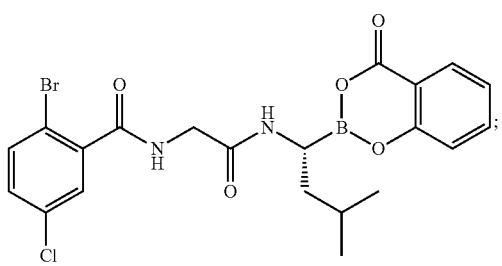

compound 8i:
2-bromo-5-chloro-N-[2-({(1R)-3-methyl-1-[(5R)-4-oxo-5-phenyl-1,3,2-dioxaborolan-2-yl]butyl}amino)-2-oxoethyl]benzamide

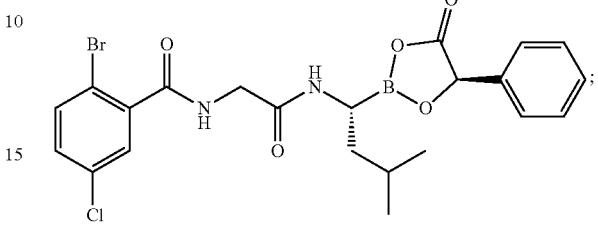

and compound 8j:
2-bromo-5-chloro-N-[2-({(1R)-3-methyl-1-[(4S)-4-methyl-5-oxo-1,3,2-dioxaborolan-2-yl]butyl}amino)-2-oxoethyl]benzamide

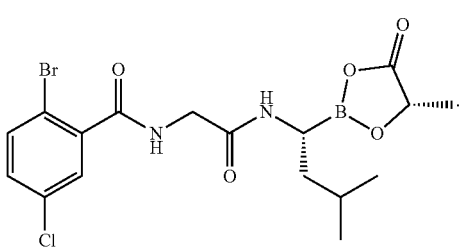

In another aspect, the present invention provides a preparation method for the compound of formula I, and the method comprises the following steps of synthesis:

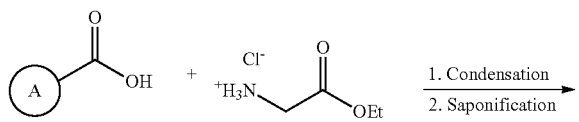

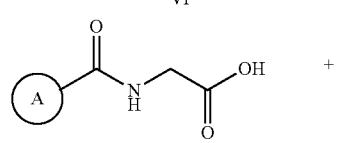

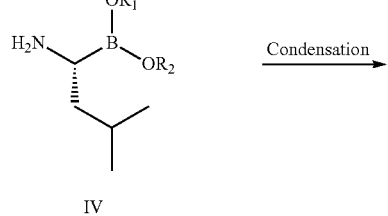

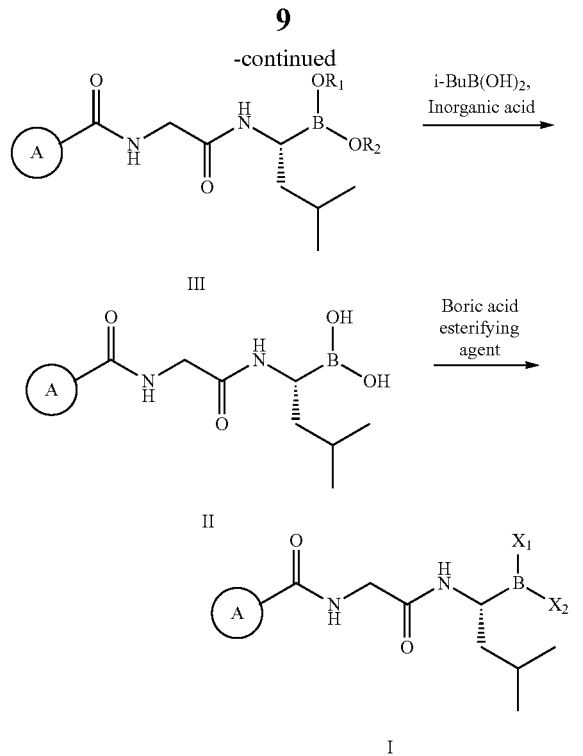

wherein, the ring A, the $X_1$ and the $X_2$ are defined according to the description above;

a) using a compound of formula VII (i.e., halogen-substituted benzoic acid) as an initial raw material, and obtaining a compound of formula V through condensation and saponification with glycine ethyl ester hydrochloride (formula VI);

b) condensing the compound of the formula V with a chiral α-aminoborate compound (formula IV) to obtain a compound of formula III, preferably, the $R_1$ and the $R_2$ in the formula IV are independently selected from a hydrogen atom, a C1-6 alkyl substituted by a substituent or unsubstituted, a C6-10 aryl substituted by a substituent or unsubstituted, a C7-18 arylalkyl substituted by a substituent or unsubstituted, a C3-15 cycloalkyl substituted by a substituent or unsubstituted, a C4-10 cycloalkyl alkyl substituted by a substituent or unsubstituted, 5-15 membered heteroaryl substituted by a substituent or unsubstituted, or a 6-21 membered heteroaryl alkyl substituted by a substituent or unsubstituted; or the $R_1$ and the $R_2$ together with a boron atom and an oxygen atom attached to the R1 and the R2 form a 5 to 10 membered carbonic ring substituted by a substituent or unsubstituted, the 5 to 10 membered carbonic ring substituted by a substituent or unsubstituted may have 0 to 2 heteroatoms selected from nitrogen, oxygen and sulfur in addition to the boron atom and the two oxygen atoms linked thereto; and the substituent is selected from the group consisting of halogens, amino, C1-6 alkyls, C2-C6 carboxyalkyls and C1-6 hydroxyalkyls and a mixture thereof;

c) hydrolyzing the compound of the formula III under a condition of inorganic acid to obtain a compound of formula II; and d) making the compound of the formula II react with the boric acid esterifying agent to obtain a compound of formula I.

In the preparation method above, the preparation method of the chiral α-aminoborate compound (the compound of the formula IV) is known in the prior art, and is recorded in, for example, CN103204867B and CN1960996B.

In the preparation method above, preferably:

a condensing agent used in the condensation reaction in the step a) is selected from the group consisting of TBTU, EDCI/HOBT and DCC/HOBT, and a reaction solvent is selected from the group consisting of dichloromethane, DMF and THF and a mixed solvent of two of dichloromethane, DMF and THF; an alkali used in the saponification reaction in the step a) is LiOH, NaOH or KOH, and is preferably NaOH, and a reaction solvent is a mixed solvent of ethanol and water;

a condensing agent used in the condensation reaction in the step b) is selected from the group consisting of TBTU, EDCI/HOBT and DCC/HOBT, and is preferably EDCI/HOBT; a reaction solvent is selected from the group consisting of dichloromethane, DMF and THF and a mixed solvent of two of dichloromethane, DMF and THF, and is preferably dichloromethane; and $R_1$ and $R_2$ in the compound of the formula IV jointly form

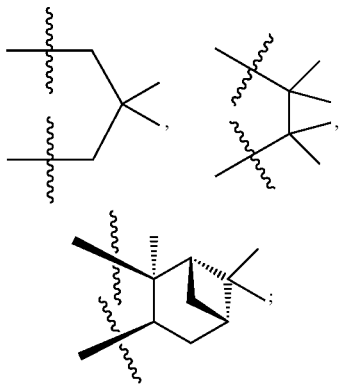

in the step c), a reaction solvent is preferably methanol/n-hexane or methanol/n-heptane; and the inorganic acid is selected from the group consisting of hydrochloric acid, sulfuric acid and nitric acid and a combination of more thereof, and is preferably hydrochloric acid; and in the step d), a reaction solvent is selected from the group consisting of ethyl acetate, THF, acetone, dichloromethane, n-hexane and heptane and a mixed solvent of two of ethyl acetate, THF, acetone, dichloromethane, n-hexane and heptane, and is preferably ethyl acetate or a mixed solvent of ethyl acetate and n-hexane; and a reaction temperature ranges from 0☐ to 100☐, and preferably ranges from 30☐ to 75☐.

Preferably, the condensation reaction in the steps a) and b) is performed in presence of organic alkali, and the organic alkali is preferably DIPEA; and preferably, in the step c), the reaction solvent is preferably a mixed solvent of methanol and n-hexane or a mixture of methanol and n-heptane.

The present invention further provides a use of the compound above in preparing medicaments for treating cancers. Preferably, the medicaments for treating cancers are proteasome inhibitor medicines. The proteasome inhibitor anti-cancer medicines include medicines for preventing and/or treating plasmacytoma, such as multiple myeloma; medicines for preventing and/or treating lymphoma, such as non-Hodgkin lymphoma, mantle cell lymphoma and/or follicular lymphoma; and medicines for preventing and treating breast cancer, colon cancer, lung cancer, kidney cancer, cervical cancer and nasopharynx cancer.

In addition, the present invention further provides a pharmaceutical composition or a pharmaceutical preparation containing the compound of the present invention. For example, the compound of the present invention may be applied in a pure form, in combination with other active ingredients, or in combination with a pharmaceutically-acceptable non-toxic excipient or carrier.

The terms used in the technical solutions of the present invention are described hereinafter.

The term "alkyl" herein refers to a saturated aliphatic hydrocarbon group having 1 to 6 carbon atoms, and the term includes straight-chain and branched-chain hydrocarbon groups. Non-limiting examples of alkyls include methyl, ethyl, n-propyl, isopropyl, n-butyl, isobutyl, sec-butyl, tert-butyl, n-pentyl, neopentyl, n-hexyl and the like.

The term "cycloalkyl" herein refers to a cyclic alkyl having 3 to 8 carbon atoms and having a single ring or multiple rings (including fused ring, bridged ring and spiral ring systems). Non-limiting examples of cycloalkyls include cyclopropyl, cyclobutyl, cyclopentyl, cyclohexyl, and the like.

The term "substitution" herein refers to that any group is monosubstituted or polysubstituted by a designated substituent to an extent that such monosubstitution or polysubstitution (including multiple substitutions in the same part) is chemically permissible, and each substituent may be located at any available position on the group and may be linked by any available atom on the substituent. The "any available position" refers to any position on the group that is chemically available by a method known in the art or taught herein, and does not produce excessively unstable molecules. When two or more substituents exist on any group, each substituent is defined independently of any other substituents, thus being the same or different. The substituent refers to a group consisting of the following groups: hydrogen, fluorine, chlorine, bromine, iodine, nitro, amino, trifluoromethyl, difluoromethyl, trifluoromethoxy, difluoromethoxy, methoxy, alkyls, acyls, alkoxys, cycloalkyls, heterocycloalkyls, carboxyalkyls, hydroxyalkyls, aryls or heteroaryls, wherein the groups are as defined herein.

The term "the compound of the present invention" (unless otherwise specifically indicated) herein refers to the compound protected by the claims and all pure nitrogen oxides, sulfur oxides, solvates, isotopic labeled compounds thereof and any pharmaceutically acceptable salts thereof. The solvate of the compound of the present invention refers to a compound combined with a stoichiometric and non-stoichiometric solvent or a salt thereof, such as a hydrate, an ethanolates, a methanolate, etc. The compound may also exist in one or more crystalline states, that is, as a eutecticum, a polymorph, or the compound may exist as an amorphous solid. All such forms are covered by the claims.

The borate compound of the present invention can further form a salt, such as the "pharmaceutically acceptable salt" derived from an inorganic or an organic acid. The salt includes but is not limited to: acetate, adipate, alginate, citrate, aspartate, benzoate, benzenesulfonate, bisulfate, butyrate, camphorate, camphorsulfonate, digluconate, cyclopentane propionate, dodecyl sulfate, ethanesulfonate, glucoheptonate, glycerophosphate, hemisulfate, heptanoate, hexanoate, fumarate, hydrochloride, hydrobromide, hydroiodate, 2-hydroxyethanesulfonate, lactate, maleate, mesylate, hydrochloride, 2-naphthalenesulfonate, oxalate, pectinate, sulfate, 3-phenylpropionate, picrate, trimethyl acetate, propionate, succinate, tartrate, thiocyanate, p-toluenesulfonate and caprate. In addition, an alkaline nitrogenous group may be subjected to quaterisation reaction with the following reagents to generate a quaternary ammonium salt: such as a lower-carbon alkyl halide, including a chloride, a bromide and an iodide of methyl, ethyl, propyl and butyl; a dialkyl sulfate, including sulfate of dimethyl, diethyl, dibutyl and dipentyl; a long-chain halide, including a chloride, a bromide and an iodide of decyl, lauryl, myristyl and stearyl; and an aralkyl halide, including a bromide of benzyl and phenethyl, etc.

The present invention further includes the isotopic labeled compound of the present invention, which has the same structure disclosed above, but one or more atoms in the structure are replaced by atoms having the same proton number but a different neutron number. The isotope embodiments combined with the compound of the present invention include isotopes of hydrogen, carbon, oxygen, sulfur, fluorine, chlorine and iodine, such as $^2H$, $^3H$, $^{13}C$, $^{14}C$, $^{15}N$, $^{18}O$, $^{17}O$, $^{35}S$, $^{18}F$, $^{36}Cl$, $^{131}I$, and the like respectively.

The term "pharmaceutically acceptable" refers to that the substance or the composition must be chemically and/or toxicologically compatible with other ingredients constituting the preparation and/or mammals treated therewith.

The "pharmaceutical preparation" mentioned in the present invention may be formed by combining the pharmaceutical composition of the present invention with a pharmaceutically acceptable adjuvant or carrier directly or further combining with other active ingredients. The preparation includes tablet, pill, capsule, granule, suspension, emulsion agent and the like. The pharmaceutically acceptable adjuvant or carrier includes: a binder such as microcrystalline cellulose, tragacanth gum or gelatin; an excipient such as starch or lactose; a dispersant such as alginic acid, Primogel or corn starch; a lubricant such as magnesium stearate; a glidant such as colloidal silicon dioxide; a sweetener such as sucrose or saccharin; a flavoring agent such as peppermint oil, methyl salicylate or an orange flavor agent; a non-aqueous solvent such as dimethyl sulfoxide, alcohol, propylene glycol, polyethylene glycol, vegetable oil such as olive oil and injectable organic ester such as ethyl oleate; an aqueous carrier such as a mixture of alcohol and water, a buffered medium and brine; as well as a preservative, an antibacterial agent, an antioxidant, a chelating agent, dye, pigment or spice.

The condensing agent TBTU in the present invention refers to O-benzotriazole-N,N,N',N'-tetramethylurea tetrafluoroborate; the condensing agent EDCI/HOBT refers to 1-(3-dimethylaminopropyl)-3-ethylcarbodiimide hydrochloride/1-hydroxybenzotriazole; and the condensing agent DCC/HOBT refers to dicyclohexylcarbodiimide/1-hydroxybenzotriazole.

The DIPEA in the present invention is diisopropylethylamine.

The solvent DMF in the present invention is dimethylformamide and the THF is tetrahydrofuran.

The "/" used between two reagents in the present invention refers to a mixture of the two reagents in front and behind.

The present invention has the following beneficial technical effects: compared with the existing borate compound used as the proteasome inhibitor, the borate compound of the present invention has the advantages of strong activity and high safety. Moreover, the borate compound of the present invention is easier to be synthesized and purified, and can effectively save production costs.

In addition, the compound of the present invention has better stability. For example, compared with compounds 8l, MLN9708, MLN2238 and the like in the prior art, the compounds 8b, 8a and the like of the present invention have better stabilities under a high-temperature and high-humidity accelerated test condition.

DETAILED DESCRIPTION OF THE INVENTION

Figure 1:
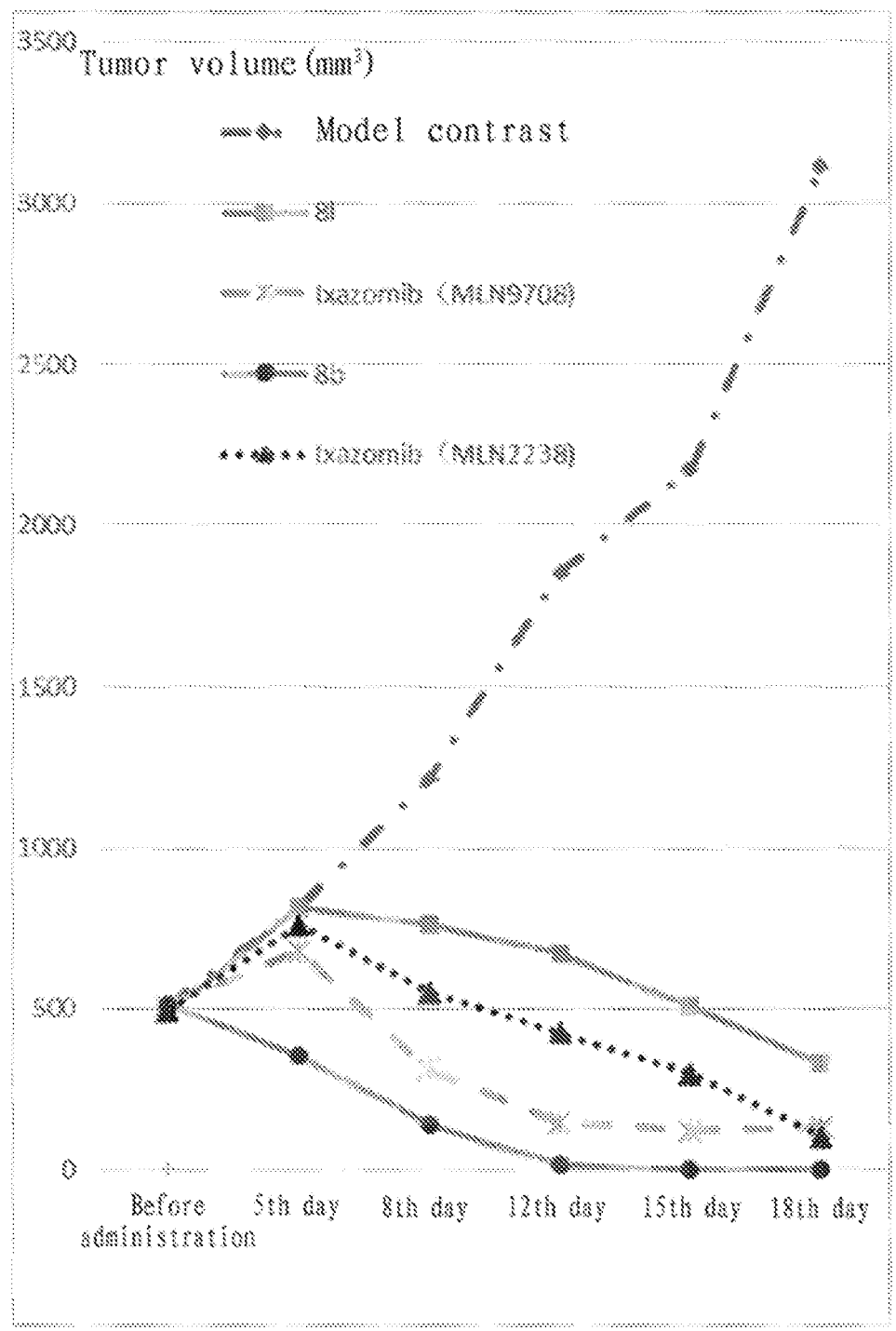
FIG. 1 shows a change of an average tumor volume of a MM.1S human multiple myeloma SCID mouse transplanted tumor model with administration time under conditions of administrations of various proteasome inhibitors.

The present invention will be further described hereinafter via the embodiments, and the implementation details of the present invention will be given. However, it should be pointed out that the embodiments described hereinafter are exemplary and are only used to explain the present invention, and should not be construed as limiting the present invention. Any modifications or replacements made by those skilled in the art according to the prior art are still included in the protection scope of the present invention.

The chemical and biological reagents used as raw materials in the specific embodiments of the present invention are commercially available.

Preparation Embodiment 1: Synthesis of Compound 3: [(2-chloro-5-bromobenzoyl)amino]ethyl Acetate

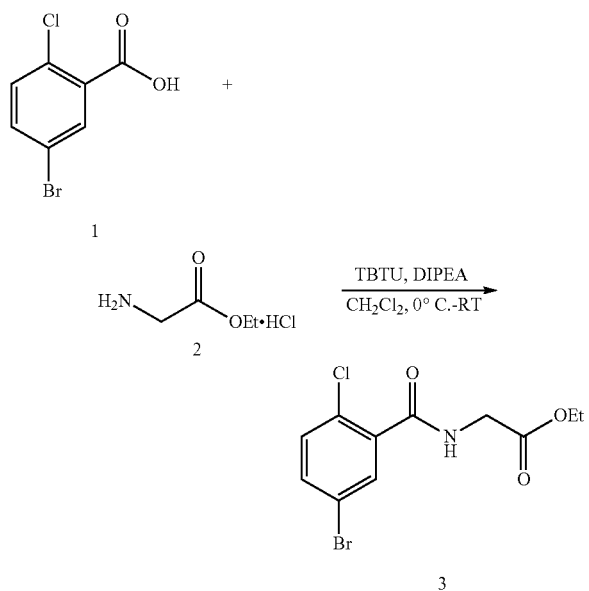

23.5 g of 2-chloro-5-bromobenzoic acid (compound 1, 100 mmol), 14.0 g of glycine ethyl ester hydrochloride (compound 2, 100 mmol) and 35.32 g of TBTU (110 mmol) were added into a 1.0 L round-bottom flask in sequence, poured into 250 mL of dichloromethane, and a mixed liquid of 38.3 ml of DIPEA (220 mmol) with 50 mL of dichloromethane was added dropwise under an ice bath condition for about 30 minutes. Then the obtained reaction mixture was gradually recovered to room temperature and reacted for 4 hours. The reaction condition was detected by TLC until the 2-chloro-5-bromobenzoic acid was completely disappeared. After the reaction was finished, the reaction mixture was washed with 300 mL of water, 200 mL of 3% $K_2CO_3$ solution, 200 ml of 2% $H_3PO_4$ solution, 200 ml of water and 150 mL of saturated saline solution in sequence, dried with 100 g of anhydrous sodium sulfate for 1 hour, and then concentrated to dryness in vacuum. A white solid product [(2-chloro-5-bromobenzoyl)amino]ethyl acetate (the compound 3) was obtained, and then the crude product was directly put into the next reaction without purification.

Preparation Embodiment 2: Synthesis of Compound 4: [(2-chloro-5-bromobenzoyl)amino]acetic Acid

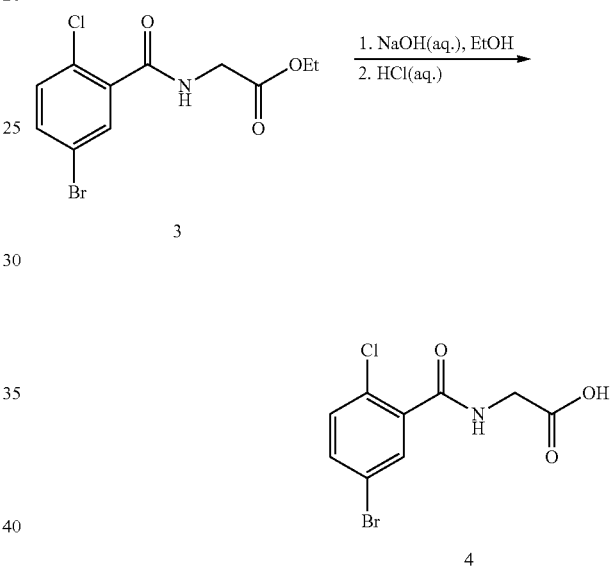

40.0 g of the crude product [(2-chloro-5-bromobenzoyl)amino]ethyl acetate (the compound 3) obtained in the previous step was added into a 1.0 L round-bottom flask, poured into 160 mL of ethanol, and then 100 mL of 2N NaOH solution (2 equivalents) was added dropwise at room temperature. The reaction condition was detected by TLC until 2-chloro-5-bromobenzoyl amino ethyl acetate was completely disappeared. After 2 hours, the reaction liquid was concentrated to one third of the volume, and then the pH was adjusted with 1N HCl solution to a weak acidity (pH was about 5). A large amount of white solid was precipitated in the system, then the reaction liquid was subjected to suction filtration, and the filter cake was washed with 200 mL×3 water for three times. After vacuum drying, a total of 23.0 g of white solid product [(2-chloro-5-bromobenzoyl)amino] acetic acid (the compound 4) could be obtained, and a total yield of the two steps was 80%. $^1$H NMR (400 MHz, DMSO) δ=8.61 (t, J=5.6 Hz, 1H), 7.65 (m, 2H), 7.47 (d, J=8.4 Hz, 1H), 5.24 (s, 3H). $^{13}$C NMR (101 MHz, DMSO) δ=171.79, 165.21, 138.70, 134.05, 132.25, 129.97, 120.16, 42.63; Melting point ranged from 1620 to 1640; and ESI-MS (m/z): [$C_9H_7BrClNO_3$—H] had a calculated value of 291.92 and a measured value of 291.77.

Preparation Embodiment 3: Synthesis of Compound 6: [(1R)-1-({[(2-chloro-5-bromo-benzoyl)amino]acetyl}amino)-3-methylbutyl]neopentyl Glycol Borate

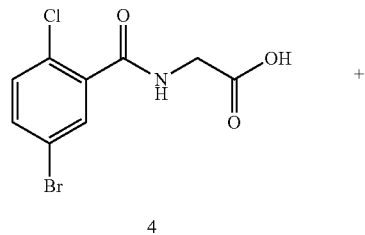

4

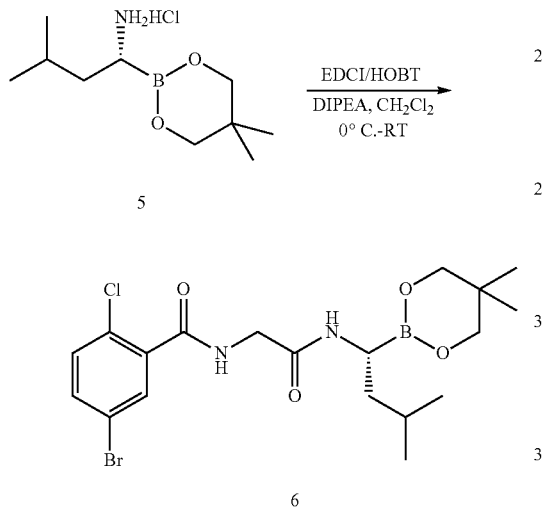

21.2 g of [(2-chloro-5-bromobenzoyl)amino]acetic acid (the compound 4, 72.5 mmol), 21.6 g of (R)-1-amino-3-methylbutane-1-boronic acid neopentyl glycol ester hydrochloride (compound 5, 79.8 mmol; the compound 5 could be prepared according to a method of an embodiment in Chinese patent CN103204867B), 16.7 g of EDCI (87.0 mmol) and 11.8 g of HOBT (87.0 mmol) were added into a 1.0 L round-bottom flask in sequence, then 250 mL of dichloromethane was poured into the round-bottom flask, and a mixed liquid of 38.3 mL of DIPEA (220 mmol) with 50 mL of dichloromethane was added dropwise under an ice bath condition for about 30 minutes. Then the obtained reaction mixture was gradually recovered to room temperature and reacted for 4 hours. The reaction condition was detected by TLC until the [(2-chloro-5-bromobenzoyl)amino]acetic acid (the compound 4) was completely disappeared. After the reaction was finished, the reaction mixture was washed with 300 mL of water, 200 mL of 3% $K_2CO_3$ solution, 200 ml of 2% $H_3PO_4$ solution, 200 ml of water and 150 mL of saturated saline solution in sequence, dried with 100 g of anhydrous sodium sulfate for 1 hour, and then concentrated to dryness in vacuum, a total of 29.5 g of white solid product [(1R)-1-({[(2-chloro-5-bromo-benzoyl)amino]acetyl}amino)-3-methylbutyl]neopentyl glycol borate (the compound 6 was obtained, with a yield of 86%, and the crude product was directly put into next reaction without purification.

Preparation Embodiment 4: Synthesis of Compound 7: [(1R)-1-({[(2-chloro-5-bromo-benzoyl)amino]acetyl}amino)-3-methylbutyl]boric Acid

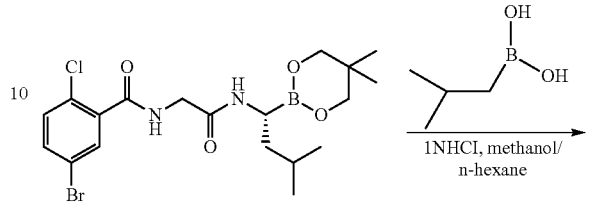

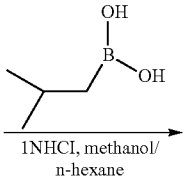

7

5.3 g of [(1R)-1-({[(2-chloro-5-bromo-benzoyl)amino]acetyl}amino)-3-methylbutyl]neopentyl glycol borate (the compound 6, 11.1 mmol) obtained in the previous step was added into a 1.0 L round-bottom flask, poured with 100 mL of mixed liquid of methanol and n-hexane in 1:1, then added with 3.6 g of isobutyl boric acid (33.3 mmol), stirred for 5 minutes, and then added with 15 mL (1.2 equivalents) of 1N HCl solution. The thus obtained reaction mixture was vigorously stirred for 4 hours, then two phases were separated, a methanol phase was washed with 100 mL×2 n-hexane twice, then the methanol phase was concentrated to a small amount, and added with 100 mL of dichloromethane, the mixed liquid was neutralized to alkaline with a 2N NaOH solution (pH was about 11) under stirring, and then extracted and separated, the water phase was washed with 100 mL×2 dichloromethane twice. Then 150 mL of dichloromethane was added into the water phase, neutralized to a weak acidity (pH was about 5) with a 1N HCl solution, and then extracted and separated, the water phase was washed with 100 mL×2 dichloromethane. Combined all of the dichloromethane phases, then washed with 150 mL of saturated saline solution once, dried with anhydrous sodium sulfate and concentrated to dryness, and dried in a vacuum drying oven at 28□, a total of 3.1 g of white solid product [(1R)-1-({[(2-chloro-5-bromo-benzoyl)amino]acetyl}amino)-3-methylbutyl]boric acid (the compound 7) was obtained, with a yield of 68%. $^1H$ NMR (400 MHz, DMSO) δ=9.03-8.93 (m, 1H), 8.75 (m, 1H), 7.83-7.76 ((d, J=4.8, 1H), 7.67 (m, 1H), 7.49 (dd, J=8.8, 4.8 Hz, 1H), 4.05 (d, J=6.4 Hz, 2H), 2.71-2.64 (m, 1H), 1.63 (m, 1H), 1.45-1.22 (m, 2H), 0.85 (dd, J=6.4, 2.0 Hz, 6H). $^{13}C$ NMR (101 MHz, DMSO) δ=171.85, 168.16, 165.65, 138.07, 134.19, 132.22, 130.08, 120.18, 55.37, 25.66, 23.43, 23.35, 22.57; and a melting point ranged from 118□ to 120□.

Preparation Embodiment 5: Synthesis of Compound 8a: 2-chloro-5-bromo-N-(2-{[(1R)-3-methyl-1-(4-oxo-4H-1,3,2-benzodioxaborolan-2-yl)butyl]amino}-2-oxoethyl)benzamide Preparation Embodiment 6: Synthesis of Compound 8b: 2-chloro-5-bromo-N-[2-({(1R)-3-methyl-1-[(5R)-4-oxo-5-phenyl-1,3,2-dioxaborolan-2-yl]butyl}amino)-2-oxoethyl]benzamide

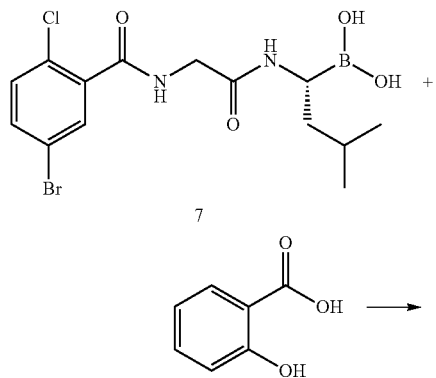

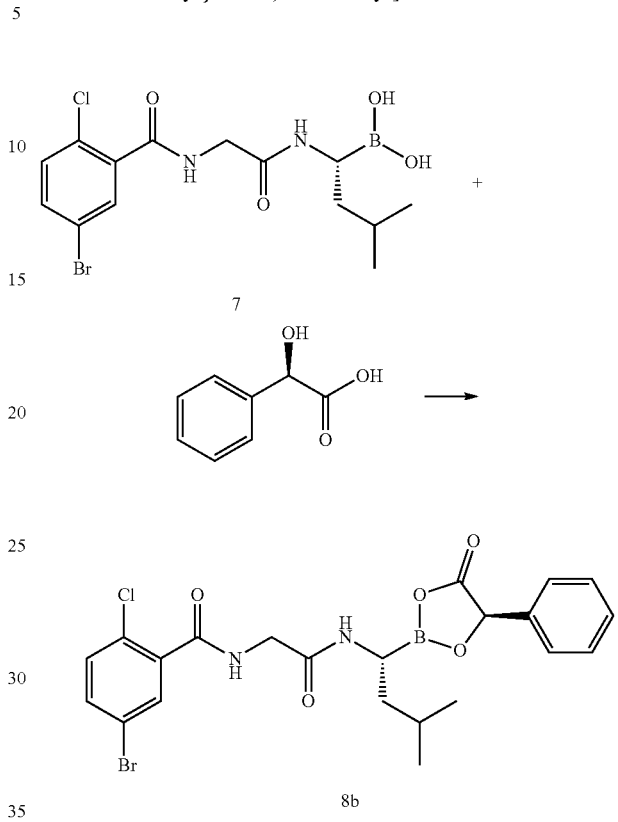

0.35 g of salicylic acid (2.5 mmol) was added into a 100 mL round-bottom flask with 10 mL of ethyl acetate, heated to 70□ to completely dissolve the salicylic acid, and then added with 1.01 g of raw material [(1R)-1-({[(2-chloro-5-bromo-benzoyl)amino]acetyl}amino)-3-methylbutyl]boric acid (the compound 7, 2.5 mmol). The obtained reaction mixture was stirred for 5 minutes, then a large amount of white solid was precipitated in the system, the reaction mixture was continuously stirred for half an hour and then cooled down to room temperature, and was subjected to suction filtration, a filter cake was washed with the ethyl acetate, and dried in vacuum, A total of 1.08 g of white solid product 2-chloro-5-bromo-N-(2-{[(1R)-3-methyl-1-(4-oxo-4H-1,3,2-benzodioxaborolan-2-yl)butyl]amino}-2-oxoethyl)benzamide (the compound 8a) was obtained, with a yield of 85%. $^1$H NMR (400 MHz, DMSO) δ=10.93 (s, 1H), 9.16 (t, J=5.6 Hz, 1H), 7.78 (dd, J=8.0, 1.6 Hz, 1H), 7.74-7.61 (m, 2H), 7.48 (m, 2H), 7.01-6.86 (m, 2H), 4.28 (d, J=5.6 Hz, 2H), 2.96-2.76 (m, 1H), 1.69 (m, 1H), 1.55-1.33 (m, 2H), 0.91 (t, J=6.4 Hz, 6H). $^{13}$C NMR (101 MHz, DMSO) δ=176.30, 166.11, 163.00, 159.01, 137.61, 135.55, 134.42, 132.24, 132.09, 130.10, 129.72, 120.27, 120.14, 118.62, 116.34, 38.87, 38.56, 26.02, 23.44, 22.57; a melting point ranged from 252□ to 254□; ESI-MS (m/z): [$C_{21}H_{21}BBrClN_2O_5$—H] had a calculated value of 507.03 and a measured value of 506.84; [$C_{21}H_{21}BBrClN_2O_5$+H$^+$] had a calculated value of 509.05 and a measured value of 508.86; and [$C_{21}H_{21}BBrClN_2O_5$+Na$^+$] had a calculated value of 531.03 and a measured value of 530.85.

0.38 g of R-mandelic acid (2.5 mmol) was added into a 100 mL round-bottom flask with 10 mL of ethyl acetate, heated to 70□ to completely dissolve the R-mandelic acid, and then added with 1.01 g of raw material [(1R)-1-({[(2-chloro-5-bromo-benzoyl)amino]acetyl}amino)-3-methylbutyl]boric acid (the compound 7, 2.5 mmol). The obtained reaction mixture was stirred for 5 minutes, then a large amount of white solid was precipitated in the system, the reaction mixture was continuously stirred for half an hour and then cooled down to room temperature, added with 10 mL of n-hexane and stirred for half an hour, and then subjected to suction filtration, a filter cake was washed with a mixed liquid of ethyl acetate and n-hexane, and dried in vacuum, a total of 1.12 g of white solid product 2-chloro-5-bromo-N-[2-({(1R)-3-methyl-1-[(5R)-4-oxo-5-phenyl-1,3,2-dioxaborolan-2-yl]butyl}amino)-2-oxoethyl]benzamide (the compound 8b) was obtained, with a yield of 86%. $^1$H NMR (400 MHz, DMSO) δ=10.91 (s, 1H), 9.24 (s, 1H), 7.81 (d, J=16.4 Hz, 1H), 7.72 (d, J=8.8 Hz, 1H), 7.56-7.26 (m, 6H), 5.30-5.11 (m, 1H), 4.37 (d, J=4.6 Hz, 2H), 2.84 (m, 1H), 1.69 (m, 1H), 1.40 (m, 2H), 0.94 (d, J=6.4 Hz, 6H). $^{13}$C NMR (101 MHz, DMSO) δ=176.83, 176.57, 166.03, 139.82, 137.47, 134.58, 132.40, 132.22, 130.22, 128.52, 127.96, 126.56, 120.24, 76.70, 60.24, 39.31, 38.74, 26.23, 23.42, 22.49, 21.23; a melting point ranged from 1700 to 1730; ESI-MS (m/z): [$C_{22}H_{23}BBrClN_2O_5$—H] had a calculated value of 521.05 and a measured value of 520.75; and [$C_{22}H_{23}BBrClN_2O_5$+Na$^+$] had a calculated value of 545.04 and a measured value of 544.76.

Preparation Embodiment 7: Synthesis of Compound 8c: 2-chloro-5-bromo-N-[2-({(1R)-3-methyl-1-[(4S)-4-methyl-5-oxo-1,3,2-dioxaborolan-2-yl]butyl}amino)-2-oxoethyl]benzamide

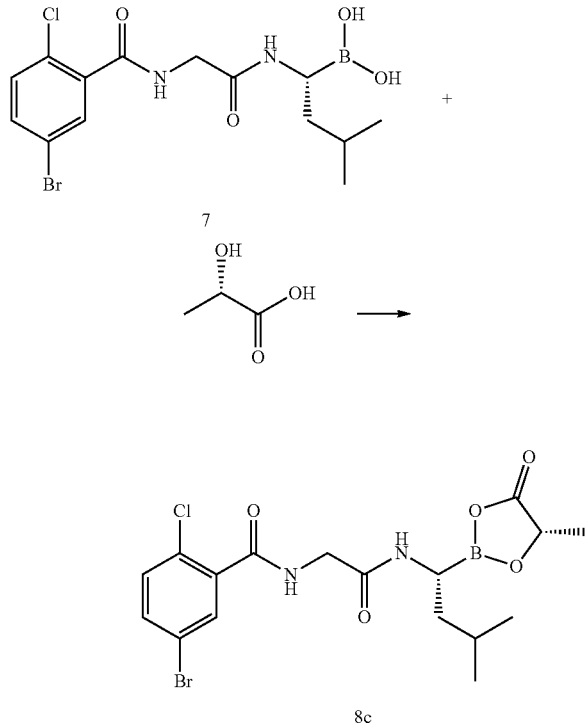

0.20 g of L-lactic acid (2.0 mmol) was added into a 100 mL round-bottom flask with 8 mL of ethyl acetate, heated to 70□ to completely dissolve the L-lactic acid, and then added with 0.81 g of raw material [(1R)-1-({[(2-chloro-5-bromo-benzoyl)amino]acetyl}amino)-3-methylbutyl]boric acid (the compound 7, 2.0 mmol). The obtained reaction mixture was stirred for 30 minutes, then the thus obtained system was clear, then the reaction mixture was added with 12 mL of n-hexane, and continuously stirred at 70□ for half an hour and then cooled down to room temperature. White solid was gradually precipitated in the system, then the reaction mixture was quickly subjected to suction filtration, a filter cake was washed with a mixed liquid of ethyl acetate and n-hexane, and dried in vacuum, a total of 0.75 g of white solid product 2-chloro-5-bromo-N-[2-({(1R)-3-methyl-1-[(4S)-4-methyl-5-oxo-1,3,2-dioxaborolan-2-yl]butyl}amino)-2-oxoethyl]benzamide (the compound 8c) was obtained, with a yield of 80%. $^1$H NMR (400 MHz, DMSO) δ=10.73 (s, 1H), 9.17 (t, J=5.6 Hz, 1H), 7.89-7.77 (m, 1H), 7.75-7.64 (m, 1H), 7.56-7.45 (m, 1H), 4.30 (d, J=5.2 Hz, 2H), 2.76-2.61 (t, J=7.2 Hz, 1H), 1.64 (d, J=5.7 Hz, 1H), 1.45-1.12 (m, 5H), 0.94-0.80 (m, 6H). $^{13}$C NMR (101 MHz, DMSO) δ=179.52, 176.28, 166.04, 137.53, 134.48, 132.29, 130.14, 120.18, 70.23, 39.28, 38.69, 25.97, 23.38, 22.55, 14.43; a melting point ranged from 135□ to 138□; ESI-MS (m/z): [$C_{17}H_{21}BBrClN_2O_5$—H] had a calculated value of 459.03 and a measured value of 458.76; and [$C_{17}H_{21}BBrClN_2O_5$+Na$^+$] had a calculated value of 483.03 and a measured value of 482.76.

Preparation Embodiment 8: Synthesis of Compound 8e: 2-bromo-5-bromo-N-(2-{[(1R)-3-methyl-1-(4-oxo-4H-1,3,2-benzodioxaborolan-2-yl)butyl]amino}-2-oxoethyl)benzamide With reference to the reaction processes in the preparation embodiments 1 to 5, only 2-chloro-5-bromobenzoic acid was replaced by 2-bromo-5-bromobenzoic acid, the rest steps were performed by reference, so as to obtain the compound 8e: 2-bromo-5-bromo-N-(2-{[(1R)-3-methyl-1-(4-oxo-4H-1,3,2-benzodioxaborolan-2-yl)butyl]amino}-2-oxoethyl)benzamide.

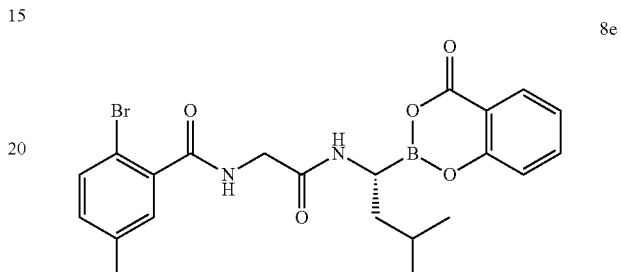

Preparation Embodiment 9: Synthesis of Compound 8f: 2-bromo-5-bromo-N-[2-({(1R)-3-methyl-1-[(5R)-4-oxo-5-phenyl-1,3,2-dioxaborolan-2-yl]butyl}amino)-2-oxoethyl]benzamide With reference to the reaction processes in the preparation embodiments 1 to 4 and the preparation embodiment 6, only 2-chloro-5-bromobenzoic acid was replaced by 2-bromo-5-bromobenzoic acid, the rest steps were performed by reference, so as to obtain the compound 8f: 2-bromo-5-bromo-N-[2-({(1R)-3-methyl-1-[(5R)-4-oxo-5-phenyl-1,3,2-dioxaborolan-2-yl]butyl}amino)-2-oxoethyl]benzamide.

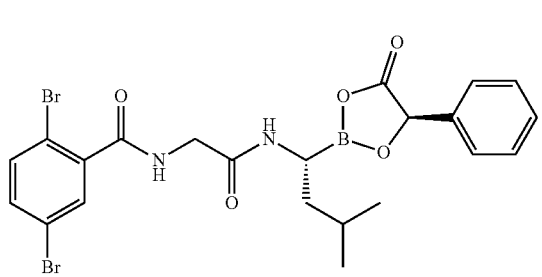

Preparation Embodiment 10: Synthesis of Compound 8g: 2-bromo-5-bromo-N-[2-({(1R)-3-methyl-1-[(4S)-4-methyl-5-oxo-1,3,2-dioxaborolan-2-yl]butyl}amino)-2-oxoethyl]benzamide With reference to the reaction processes in the preparation embodiments 1 to 4 and the preparation embodiment 7, only 2-chloro-5-bromobenzoic acid was replaced by 2-bromo-5-bromobenzoic acid, the rest steps were performed by reference, so as to obtain the compound 8g: 2-bromo-5-bromo-N-[2-({(1R)-3-methyl-1-[(4S)-4-methyl-5-oxo-1,3,2-dioxaborolan-2-yl]butyl}amino)-2-oxoethyl]benzamide.

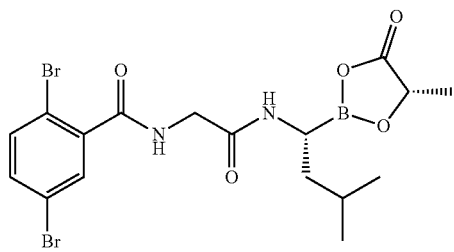

8g

Preparation Embodiment 11: Synthesis of Compound 8h: 2-bromo-5-chloro-N-(2-{[(1R)-3-methyl-1-(4-oxo-4H-1,3,2-benzodioxaborolan-2-yl)butyl]amino}-2-oxoethyl)benzamide With reference to the reaction processes in the preparation embodiments 1 to 5, only 2-chloro-5-bromobenzoic acid was replaced by 2-bromo-5-chlorobenzoic acid, the rest steps were performed by reference, so as to obtain the compound 8h: 2-bromo-5-chloro-N-(2-{[(1R)-3-methyl-1-(4-oxo-4H-1,3,2-benzo dioxaborolan-2-yl)butyl]amino}-2-oxoethyl)benzamide.

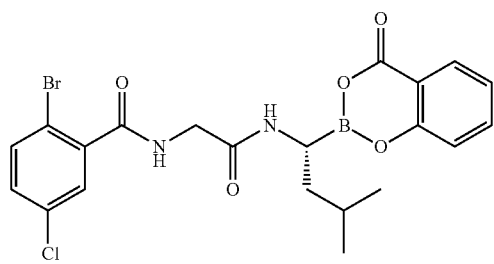

8h

Preparation Embodiment 12: Synthesis of Compound 8i: 2-bromo-5-chloro-N-[2-({(1R)-3-methyl-1-[(5R)-4-oxo-5-phenyl-1,3,2-dioxaborolan-2-yl]butyl}amino)-2-oxoethyl]benzamide With reference to the reaction processes in the preparation embodiments 1 to 4 and the preparation embodiment 6, only 2-chloro-5-bromobenzoic acid was replaced by 2-bromo-5-chlorobenzoic acid, the rest steps were performed by reference, so as to obtain the compound 8i: 2-bromo-5-chloro-N-[2-({(1R)-3-methyl-1-[(5R)-4-oxo-5-phenyl-1,3,2-dioxaborolan-2-yl]butyl}amino)-2-oxoethyl]benzamide.

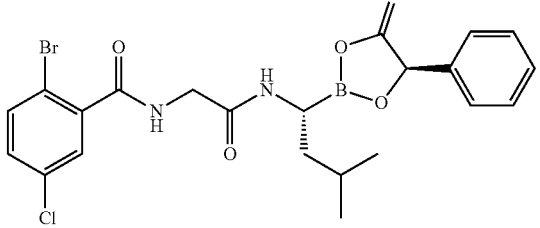

8i

Preparation Embodiment 13: Synthesis of Compound 8j: 2-bromo-5-chloro-N-[2-({(1R)-3-methyl-1-[(4S)-4-methyl-5-oxo-1,3,2-dioxaborolan-2-yl]butyl}amino)-2-oxoethyl]benzamide With reference to the reaction processes in the preparation embodiments 1 to 4 and the preparation embodiment 7, only 2-chloro-5-bromobenzoic acid was replaced by 2-bromo-5-chlorobenzoic acid, the rest steps were performed by reference, so as to obtain the compound 8j: 2-bromo-5-chloro-N-[2-({(1R)-3-methyl-1-[(4S)-4-methyl-5-oxo-1,3,2-dioxaborolan-2-yl]butyl}amino)-2-oxoethyl]benzamide.

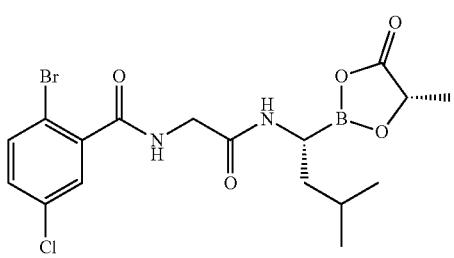

8j

Preparation Embodiment 14: Synthesis of Compound 8m: 2-chloro-5-bromo-N-[2-({(1R)-3-methyl-1-[(5S)-4-oxo-5-phenyl-1,3,2-dioxaborolan-2-yl]butyl}amino)-2-oxoethyl]benzamide

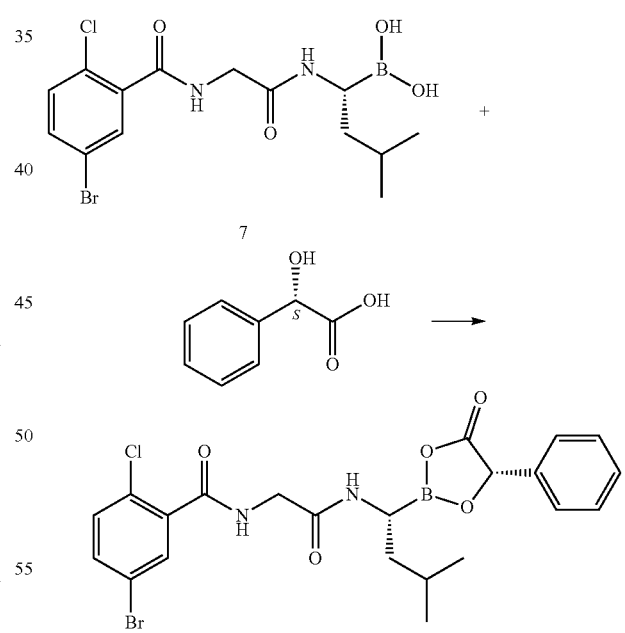

8m 0.31 g of S-mandelic acid (2.0 mmol) was added into a 100 mL round-bottom flask with 10 mL of ethyl acetate, heated to 70□ to completely dissolve the S-mandelic acid, and then added with 0.81 g of raw material [(1R)-1-({[(2-chloro-5-bromo-benzoyl)amino]acetyl}amino)-3-methyl-butyl]boric acid (the compound 7, 2.0 mmol). The obtained reaction mixture was stirred for 5 minutes, then a large amount of white solid was precipitated in the obtained system, the reaction mixture was continuously stirred for half an hour and then cooled down to room temperature, added with 10 mL of n-hexane and stirred for half an hour, and then was subjected to suction filtration, a filter cake was washed with a mixed liquid of ethyl acetate and n-hexane, and dried in vacuum, a total of 0.73 g of white solid product 2-chloro-5-bromo-N-[2-({(1R)-3-methyl-1-[(5 S)-4-oxo-5-phenyl-1,3,2-dioxaborolan-2-yl]butyl}amino)-2-oxoethyl]benzamide (the compound 8m) was obtained, with a yield of 70%. $^1$H NMR (400 MHz, DMSO) δ=10.92 (s, 1H), 9.25 (s, 1H), 7.84 (d, J=24.0 Hz, 1H), 7.72 (d, J=8.0, 1H), 7.52 (d, J=8.0 Hz, 2H), 7.46-7.23 (m, 4H), 5.20 (d, J=40.0 Hz, 1H), 4.38 (d, J=2.8 Hz, 2H), 2.87 (m, 1H), 1.92-1.54 (m, 1H), 1.41 (m, 2H), 0.92 (d, J=6.4 Hz, 6H).

Preparation Embodiment 15: Synthesis of Compound 8n: 2-chloro-5-bromo-N-[2-({(1R)-3-methyl-1-[4-oxo-5-phenyl-1,3,2-dioxaborolan-2-yl]butyl}amino)-2-oxoethyl]benzamide

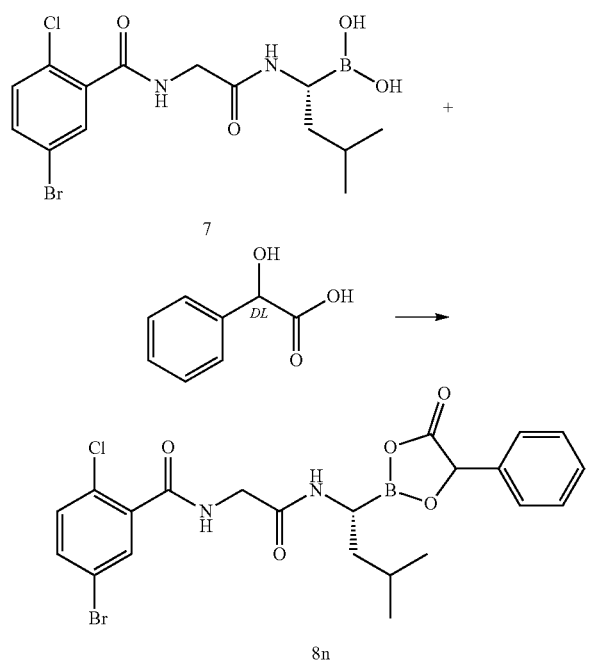

0.31 g of DL-mandelic acid (2.0 mmol) was added into a 100 mL round-bottom flask with 10 mL of ethyl acetate, heated to 70□ to completely dissolve the DL-mandelic acid, and then added with 0.81 g of raw material [(1R)-1-({[(2-chloro-5-bromo-benzoyl)amino]acetyl}amino)-3-methylbutyl]boric acid (the compound 7, 2.0 mmol). The obtained reaction mixture was stirred for 5 minutes, then a large amount of white solid was precipitated in a system, the reaction mixture was continuously stirred for half an hour and then cooled down to room temperature, added with 10 mL of n-hexane and stirred for half an hour, and then was subjected to suction filtration, a filter cake was washed with a mixed liquid of the ethyl acetate and the n-hexane, and dried in vacuum, a total of 0.75 g of white solid product 2-chloro-5-bromo-N-[2-({(1R)-3-methyl-1-[4-oxo-5-phenyl-1,3,2-dioxaborolan-2-yl]butyl}amino)-2-oxoethyl]benzamide (the compound 8n) was obtained, with a yield of 72%. $^1$H NMR (400 MHz, DMSO) δ=10.92 (s, 1H), 9.25 (s, 1H), 7.92-7.76 (m, 1H), 7.72 (d, J=8.0 Hz, 1H), 7.52 (d, J=8.0 Hz, 2H), 7.47-7.25 (m, 4H), 5.19 (m, 1H), 4.37 (d, J=4.0 Hz, 2H), 3.00-2.73 (m, 1H), 1.70 (m, 1H), 1.57-1.26 (m, 2H), 0.92 (d, J=6.4 Hz, 6H).

Preparation Comparison 1: Synthesis of Compound 8d: 2-chloro-5-bromo-N-(2-{[(1R)-1,3,5,2-dioxaborolan-2-yl)-3-methylbutyl]amino}-2-oxoethyl) benzamide

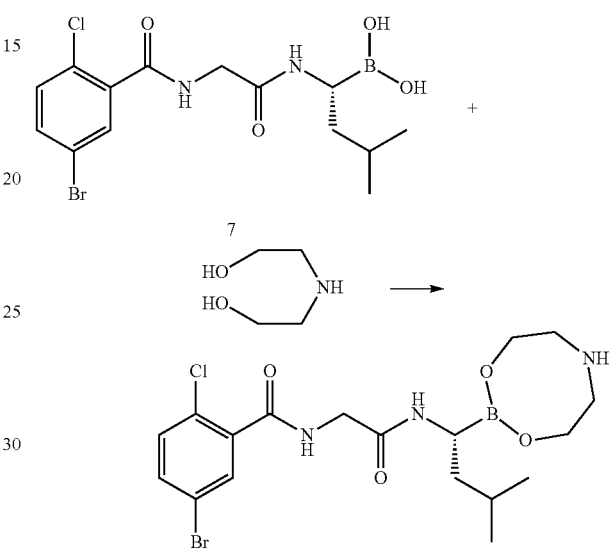

1.01 g of raw material [(1R)-1-({[(2-chloro-5-bromobenzoyl)amino]acetyl}amino)-3-methylbutyl]boric acid (the compound 7, 2.5 mmol) was added into a 100 ml round-bottom flask under room temperature with 10 mL of ethyl acetate for dissolution, and then added with 0.27 g of diethanolamine (2.5 mmol). The obtained reaction mixture was stirred for 5 minutes, then a large amount of white solid was precipitated in a system, the reaction mixture was continuously stirred for half an hour, and then was subjected to suction filtration, a filter cake was washed with ethyl acetate, and dried in vacuum, a total of 1.08 g of white solid product 2-chloro-5-bromo-N-(2-{[(1R)-1,3,5,2-dioxaborolan-2-yl)-3-methylbutyl]amino}-2-oxoethyl)benzamide (the compound 8d) was obtained, with a yield of 88%. $^1$H NMR (400 MHz, DMSO) δ=8.85 (t, J=6.0 Hz, 1H), 7.73-7.60 (m, 2H), 7.50 (d, J=8.4 Hz, 1H), 7.00 (d, J=8.4 Hz, 1H), 6.59 (s, 1H), 3.90-3.63 (m, 5H), 3.63-3.54 (m, 1H), 3.15 (m, 1H), 3.05-2.90 (m, 2H), 2.84-2.66 (m, 2H), 1.68-1.50 (m, 1H), 1.40-1.27 (m, 1H), 1.20 (m, 1H), 0.88-0.75 (dd, J=6.4 Hz, J=10.8 Hz, 6H). $^{13}$C NMR (101 MHz, DMSO) δ=168.21, 165.63, 138.58, 134.15, 132.23, 131.95, 129.91, 120.24, 62.94, 51.39, 50.96, 43.31, 25.00, 24.44, 22.14; a melting point ranged from 2170 to 218.

The material of diethanolamine was difficult to be completely removed in post-treatment and was easy to remain in the product 8d. Meanwhile, the compound 8d could be hydrolyzed, which was easy to hydrolyze in vivo to produce diethanolamine. The diethanolamine is a class II carcinogen (http://www.sda.gov.cn/WS01/CL1991/215896.html) released by the World Health Organization.

Preparation Comparison 2: Synthesis of Compound 8k: 2-bromo-5-chloro-N-(2-{[(1R)-1,3,5,2-dioxaborolan-2-yl)-3-methylbutyl]amino}-2-oxoethyl)benzamide

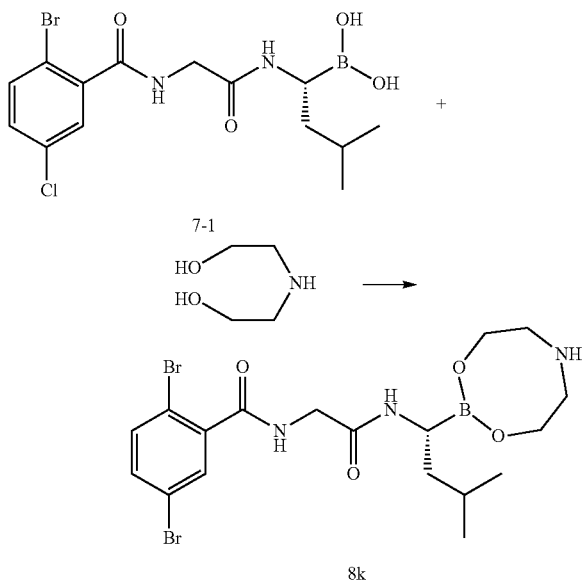

1.22 g of raw material [(1R)-1-({[(2-bromo-5-chloro-benzoyl)amino]acetyl}amino)-3-methylbutyl]boric acid (compound 7-1, 3.0 mmol) was added into a 100 ml round-bottom flask under room temperature, added with 20 mL of ethyl acetate for dissolution, and then added with 0.315 g of diethanolamine (3.0 mmol). The obtained reaction mixture was stirred for 5 minutes, then a large amount of white solid was precipitated in the obtained system, the reaction mixture was continuously stirred for half an hour, and then was subjected to suction filtration, a filter cake was washed with the ethyl acetate, and dried in vacuum, a total of 1.20 g of white solid product 2-bromo-5-chloro-N-(2-{[(1R)-1,3,5,2-dioxaborolan-2-yl)-3-methylbutyl]amino}-2-oxoethyl)benzamide (the compound 8k) was obtained, with a yield of 84%. $^1$H NMR (400 MHz, DMSO) δ=8.85 (t, J=6.0 Hz, 1H), 7.71 (d, J=8.4 Hz, 1H), 7.60-7.40 (m, 2H), 7.03 (d, J=8.4 Hz, 1H), 6.60 (s, 1H), 3.89-3.64 (m, 5H), 3.63-3.53 (m, 1H), 3.16 (m, 1H), 3.09-2.92 (m, 2H), 2.86-2.65 (m, 2H), 1.70-1.53 (m, 1H), 1.43-1.28 (m, 1H), 1.20 (m, 1H), 0.82 (dd, J=11.2, 6.8 Hz, 6H).

Preparation Comparison 3: Synthesis of Compound 8l: 2-chloro-5-chloro-N-[2-({[(1R)-3-methyl-1-[(5R)-4-oxo-5-phenyl-1,3,2-dioxaborolan-2-yl]butyl}amino)-2-oxoethyl]benzamide

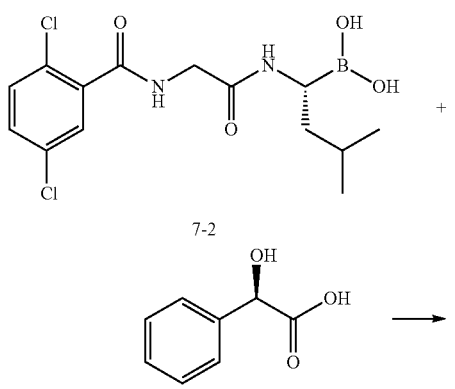

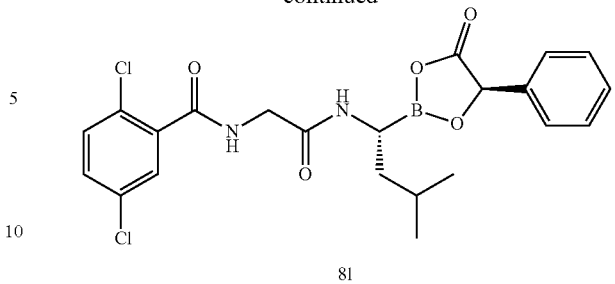

0.46 g of R-mandelic acid (3.0 mmol) was added into a 100 mL round-bottom flask with 10 mL of ethyl acetate, heated to 70□ to completely dissolve the R-mandelic acid, and then added with 1.08 g of raw material [(1R)-1-({[(2-chloro-5-chloro-benzoyl)amino]acetyl}amino)-3-methyl-butyl]boric acid (compound 7-2, 3.0 mmol). The obtained reaction mixture was stirred for 10 minutes, a large amount of white solid was precipitated in the obtained system, the reaction mixture was continuously stirred for half an hour and then cooled down to room temperature, added with 10 mL of n-hexane and stirred for half an hour, and then was subjected to suction filtration, a filter cake was washed with a mixed liquid of the ethyl acetate and the n-hexane, and dried in vacuum, a total of 0.81 g of white solid product 2-chloro-5-chloro-N-[2-({[(1R)-3-methyl-1-[(5R)-4-oxo-5-phenyl-1,3,2-dioxaborolan-2-yl]butyl}amino)-2-oxoethyl]benzamide (the compound 8l) was obtained, with a yield of 57%. $^1$H NMR (400 MHz, DMSO) δ=10.90 (s, 1H), 9.24 (s, 1H), 7.79-7.56 (m, 3H), 7.54-7.21 (m, 5H), 5.19 (s, 1H), 4.36 (d, J=5.2 Hz, 2H), 2.82 (m, 1H), 1.68 (m, 1H), 1.39 (m, 2H), 0.93 (d, J=6.8 Hz, 6H).

Experimental Embodiment 1: In Vitro Activity Test

Cells RPMI-8226 (human multiple myeloma cell) and MM.1S (human multiple myeloma cell) were cultured in a RPMI 1640 medium containing 10% fetal bovine serum at 37□ under 5% $CO_2$ to a logarithmic growth phase. The cells were respectively inoculated into a 96-well culture plate in a quantity of $3\times10^4$/well. After culturing for 24 hours at 37□ under 5% $CO_2$, a solvent control DMSO (dimethyl sulfoxide) or a tested compound (the tested compound taken 0.3 μM as an initial concentration, was diluted 3 times each time, and was diluted 5 times in total to obtain 6 concentration gradients) dissolved in the DMSO was added into the cells. The tested compound was incubated with the cells for 48 hours at 37□ under 5% $CO_2$. A CCK-8 reagent was added into each well, and incubated at 37□ for 2 hours according to a reagent specification, and an optical density value of each well was read at a wavelength of 450 nm using a spectrophotometer.

An optical density value of the cells when the medicine acted for 0 hour was set as a Tz value, which represented a value of the cells when the medicine was added. The optical density value of the cells when the solvent control DMSO acted for 48 hours was set as a C value; and the optical density value of the cells when the tested compound acted for 48 hours was set as a Ti value. According to a method proposed by the NIH-NCI (National Institutes of Health-National Cancer Institute) of the United States, a response of the cells to a medicine was calculated: when Ti≥Tz, the response was [(Ti−Tz)/(C−Tz)]×100; and when Ti<Tz, the response was [(Ti−Tz)/Tz]×100. According to the calculation above, a GI50 value (a concentration of the tested compound required when a cell growth inhibition rate was 50%) was calculated by the 4 Parameter Logistic Model in the XLfit software. Activity data were shown in Table 1 below.

TABLE 1

| | In Vitro Activity Test Results | |
|---|---|---|
| Compound | RPMI 8226 cell GI50 (μM) value | MM.IS cell GI50 (μM) value |
| 8a | 0.006185 | 0.002089 |
| 8b | 0.005982 | 0.002753 |
| 8d | 0.006511 | 0.007126 |
| 8k | 0.005998 | 0.008164 |
| 8l | 0.02156 | 0.01861 |

TABLE 1-continued

In Vitro Activity Test Results

| Compound | RPMI 8226 cell GI50 (μM) value | MM.IS cell GI50 (μM) value |
|---|---|---|
| [structure with 2,5-dichlorobenzamide-Gly-Leu-boronate with dioxaborinane-diCOOH] | 0.011623 | 0.006477 |
| Or [structure MLN9708: 2,5-dichlorobenzamide-Gly-Leu-boronate with dioxaborolane-diCOOH] | | |

Experimental Embodiment 2: Pharmacodynamic Test

In the experiment, a SCID mouse transplanted tumor model of a human multiple myeloma cell line MM.1S was used. Specific modeling steps were as follows: frozen MM.1S cells were resuscitated and cultured in vitro according to a routine, and the cells were collected in a logarithmic growth phase, and diluted with PBS to form a tumor cell suspension with a concentration of $5 \times 10^7$/ml. The prepared tumor cell suspension above was injected subcutaneously to a side of an armpit close to a back of a 5-week-old SCID mouse, the mouse had a weight ranging from 16 g to 18 g and was female, and 0.2 ml of the suspension was injected at each inoculation site. About 1 week to 2 weeks after injection, the mass was palpable in axillary, and in vivo passage was performed when a tumor volume was larger than 500 mm$^3$. After the mouse was killed by a neck pulling method, a body surface was disinfected, skin was cut open, aseptic operation was performed, a tumor tissue was peeled off from an axillary subcutaneous tissue, a fibrous capsule was removed, and the tumor was taken out. The tumor was washed clean in normal saline, and then cut, and after removing the central necrotic part, the tumor tissue with good growth, reddish color and fish flesh shape was selected, then was cut into 1 mm×1 mm×1 mm small pieces, and placed in normal saline for later use. The cut tumor was placed in a mouth of a No. 18 trocar, iodized cotton was used to disinfect the side of the armpit close to the back of the mouse, and local inoculation was performed. The transplanted tumor used in the test was the 4$^{th}$ generation of in vivo passage. When the tumor volume of most SCID mice of in vivo passage was larger than 100 mm$^3$, the tumor volume was measured and calculated, and the mice were randomly grouped according to the tumor volume.

The administration mode was intragastric administration through mouth, with an administration volume of 10 ml/kg. The model control group was given the same volume of solvent intragastrically. The mice were all intragastrically administrated through mouth twice a week for a total of 5 times, i.e., the mice were administrated at the 1$^{st}$, 5$^{th}$, 8$^{th}$, 12$^{th}$ and 15$^{th}$ days of the experiment, with a duration of 18 days.

Doses of different tested samples were equimolar, with a specific dose of 0.0166 mmol/kg; and the model control group was only given normal saline. The medicines were 8b and 8l, as well as Ixazomib Citrate (MLN9708) and Ixazomib (MLN2238).

On the 5$^{th}$, 8$^{th}$, 12$^{th}$, 15$^{th}$ and 18$^{th}$ days after administration, a short diameter (a) and a long diameter (b) of the tumor of each mouse were measured with a vernier caliper, and the tumor volume was calculated according to a formula ($a^2 \times b$)/2. A relative tumor volume (RTV) was calculated based on the tumor volume measured and calculated, RTV=$V_t/V_0$. $V_0$ was the tumor volume at random grouping (i.e., $d_0$) and $V_t$ was the tumor volume at each measurement (i.e., $d_n$). A relative tumor proliferation rate of an anti-tumor activity evaluation index was calculated according to the following formula: relative tumor proliferation rate T/C (%):

$$T/C\% = \frac{T_{RTV}}{C_{RTV}} \times 100\%.$$

(Note: $T_{RTV}$ was a RTV of the treatment group; and $C_{RTV}$ was a RTV of the model control group. An evaluation standard of a curative effect was T/C %≤40%, and the medicine was effective when P<0.05 after statistical treatment).

After weighing and measuring the tumor on the 18$^{th}$ day, all animals were sacrificed, and the tumor was taken and weighed.

FIG. 1 showed a change of an average tumor volume of a MM.1S human multiple myeloma SCID mouse transplanted tumor model with administration time under a condition of administration of various proteasome inhibitors. It could be seen that an initial average tumor volume was about 500 mm³ before administration. The average relative tumor volume (RTV) and the relative tumor proliferation rate T/C (%) of each group during the test were given in Tables 2 and 3 respectively.

It could be seen from the results that the compound 8b of the present invention significantly inhibited tumor growth of the MM. 1S human multiple myeloma SCID mouse transplanted tumor, and an effect of inhibiting tumor growth was

TABLE 2

Average Tumor Relative Volume of MM. 1S Human Multiple Myeloma SCID Mouse Transplanted Tumor Model under Resistance of Proteasome Inhibitor ($\overline{X} \pm SD$) (RVT = $V_d/V_0$, $V_0$ was a volume before administration, and $V_d$ was a volume on the $d^{th}$ day)

| Group | 5$^{th}$ day RVT$_5$ | 8$^{th}$ day RVT$_8$ | 12$^{th}$ day RVT$_{12}$ | 15$^{th}$ day RVT$_{15}$ | 18$^{th}$ day RVT$_{18}$ |
|---|---|---|---|---|---|
| Model control | 1.734 ± 0.489★★ | 2.725 ± 0.850★★ | 3.989 ± 1.010★★ | 4.849 ± 1.429★★ | 6.698 ± 1.396★★ |
| 8b | 0.792 ± 0.400▲▲ | 0.330 ± 0.296▲▲ | 0.034 ± 0.012▲▲ | 0.008 ± 0.004▲▲ | 0.002 ± 0.003▲▲ |
| Ixazomib (MLN9708) | 1.431 ± 0.452★★ | 0.571 ± 0.305▲▲ | 0.245 ± 0.123★★▲▲ | 0.214 ± 0.133★★▲▲ | 0.205 ± 00.151★★▲▲ |
| Ixazomib (MLN2238) | 1.522 ± 0.273★★ | 1.238 ± 0.841★★▲▲ | 0.898 ± 0.749★★▲▲ | 0.489 ± 0.343★★▲▲ | 0.163 ± 0.132★★▲▲ |
| 8l | 1.791 ± 0.540★★ | 1.739 ± 0.783★★▲ | 1.451 ± 0.676★★▲▲ | 1.127 ± 0.667★★▲▲ | 0.561 ± 0.468★★▲▲ |

Note:
▲compared with the model control group in the same period p < 0.05, ▲▲compared with the model control group in the same period p < 0.01, ★compared with the 8b group in the same period p < 0.05, and ★★compared with the 8b group in the same period p < 0.01.

TABLE 3

Relative Tumor Proliferation Rate T/C(%) of MM.1S Human Multiple Myeloma SCID Mouse Transplanted Tumor Model under Resistance of Proteasome Inhibitor (T/C(%) = RVT$_T$/RVT$_C$, RVT$_T$ was the average relative tumor volume of the administration group, and RVT$_C$Vd was the average relative tumor volume of the model control group in the same period)

| Group | 5th day T/C(%) | 8h day T/C(%) | 12th day T/C(%) | 15th day T/C(%) | 18th day T/C(%) |
|---|---|---|---|---|---|
| 8b | 45.67 | 12.11 | 0.85 | 0.17 | 0.03 |
| Ixazomib (MLN9708) | 82.56★★ | 20.94 | 6.13★★ | 4.42★★ | 3.06★★ |
| Ixazomib (MLN2238) | 87.8★★ | 45.44★ | 22.51★★ | 10.8★★ | 2.43★★ |
| 8l | 103.30★★ | 63.82★★ | 36.37★★ | 23.24★★ | 8.38★ |

Note:
★compared with the 8b group in the same period p < 0.05, and ★★compared with the 8b group in the same period p < 0.01.

Table 4 showed an average tumor weight of each group after the 18$^{th}$ day of administration.

Figure 2:
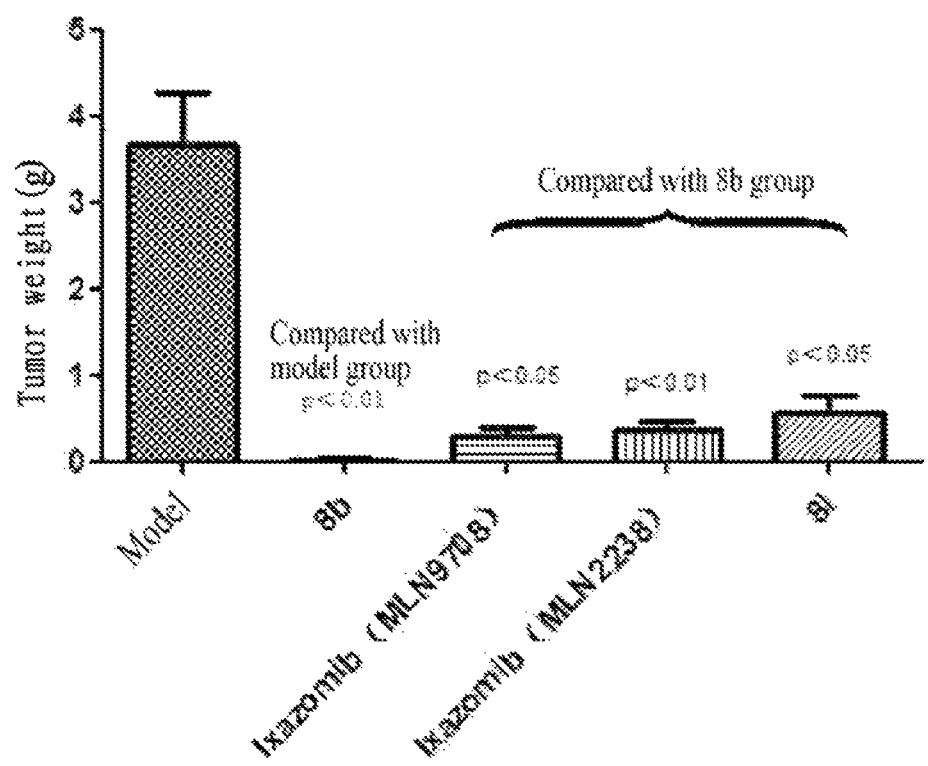
FIG. 2 shows an average tumor weight of the MM.1S human multiple myeloma SCID mouse transplanted tumor model under resistances of various proteasome inhibitors.

FIG. 2 showed a comparison histogram of an average tumor weight of each group.

TABLE 4

Average Tumor Weight of MM.1S Human Multiple Myeloma SCID Mouse Transplanted Tumor Model under Resistance of Proteasome Inhibitor ($\overline{X} \pm SD$, g)

| Group | Tumor weight (g) |
|---|---|
| Model control | 3.675 ± 1.786★★ |
| 8b | 0.028 ± 0.025 |
| Ixazomib (MLN9708) | 0.284 ± 0.312★ |
| Ixazomib (MLN2238) | 0.374 ± 0.291★★ |
| 8l | 0.560 ± 0.566★ |

Note:
★compared with the 8b group p < 0.05, and ★★compared with the 8b group p < 0.01.

significantly stronger than that of the comparative compound 8l (p<0.01), the Ixazomib (MLN9708) (p<0.01) and the Ixazomib active form (MLN2238) (p<0.01), with significant difference.

Experimental Embodiment 3: Safety Test

The test was a single-dose toxicity test of SD rats by intragastric administration through mouth. 252 SD rats were randomly grouped into 21 groups by weight, with 12 rats in each group, half male and half female. The groups were respectively a solvent control group, MLN2238 dose groups 1, 2, 3 and 4, MLN9708 dose groups 1, 2, 3 and 4, 8l dose groups 1, 2, 3 and 4, 8d dose groups 1, 2, 3 and 4, and 8b dose groups 1, 2, 3 and 4. The dose groups with the same serial number of different tested samples had the same molar dose, and doses of the dose groups 1, 2, 3 and 4 were respectively 0.001108 mmol/kg, 0.001662 mmol/kg, 0.002216 mmol/kg and 0.00277 mmol/kg. The rats in each group were administrated intragastrically once, and were recovered and observed for 14 days after medicine withdrawal, and death of the rats was shown in Table 5.

TABLE 5

Single-dose Toxicity Test Grouping of SD Rats Administrated Proteasome Inhibitor Intragastrically through mouth and Survival of Rats

| Group | Dose* (mmol/kg) | Female Death | Female Suvival | Male Death | Male Suvival |
|---|---|---|---|---|---|
| Solvent control group | — | 0 | 6 | 0 | 6 |
| MLN2238 dose 1 | 0.001108 | 0 | 6 | 0 | 6 |
| MLN2238 dose 2 | 0.001662 | 2 | 4 | 0 | 6 |
| MLN2238 dose 3 | 0.002216 | 4 | 2 | 0 | 6 |
| MLN2238 dose 4 | 0.00277 | 6 | 0 | 0 | 6 |
| MLN9708 dose 1 | 0.001108 | 0 | 6 | 0 | 6 |
| MLN9708 dose 2 | 0.001662 | 1 | 5 | 0 | 6 |
| MLN9708 dose 3 | 0.002216 | 3 | 3 | 0 | 6 |
| MLN9708 dose 4 | 0.00277 | 6 | 0 | 0 | 6 |

TABLE 5-continued

Single-dose Toxicity Test Grouping of SD Rats Administrated Proteasome Inhibitor Intragastrically through mouth and Survival of Rats

| Group | Dose* (mmol/kg) | Female Death | Female Suvival | Male Death | Male Suvival |
|---|---|---|---|---|---|
| 8l dose 1 | 0.001108 | 0 | 6 | 0 | 6 |
| 8l dose 2 | 0.001662 | 1 | 5 | 0 | 6 |
| 8l dose 3 | 0.002216 | 2 | 4 | 0 | 6 |
| 8l dose 4 | 0.00277 | 6 | 0 | 0 | 6 |
| 8d dose 1 | 0.001108 | 0 | 6 | 0 | 6 |
| 8d dose 2 | 0.001662 | 2 | 4 | 0 | 6 |
| 8d dose 3 | 0.002216 | 5 | 1 | 0 | 6 |
| 8d dose 4 | 0.00277 | 6 | 0 | 0 | 6 |
| 8b dose 1 | 0.001108 | 0 | 6 | 0 | 6 |
| 8b dose 2 | 0.001662 | 0 | 6 | 0 | 6 |
| 8b dose 3 | 0.002216 | 0 | 6 | 0 | 6 |
| 8b dose 4 | 0.00277 | 2 | 4 | 0 | 6 |

It could be seen from the results that in female rats, a maximum tolerance dose of 8b was 0.002216 mmol/kg, while a maximum tolerance dose of Ixazomib (MLN2238), Ixazomib (MLN9708), 8l and 8k was 0.001108 mmol/kg, which was significantly lower than that of 8b, and the difference was statistically significant (p<0.01).

Experimental Embodiment 4: Inhibition Test of hERG Potassium Channel of Heart

A patch clamp technique was used to detect a concentration-effect relationship of a blocking effect of tested samples (compounds 8a and 8b) on a hERG potassium channel, so as to evaluate a risk of the sample inhibiting a hERG potassium channel of a heart. An inhibitory effect of the tested compound on hERG was judged by a general standard (Roche O. et al. ChemBioChem. 2002, 3:455-459.):

Very strong inhibition: IC50<0.1 µM; strong inhibition: 0.1 µM≤IC50≤1 µM; moderate inhibition: 1 µM≤IC50≤10 µM; and weak inhibition or no inhibition: IC50>10 µM.

Generally, patch clamp study was a sensitive index to predict a risk of QT interval prolongation caused by a compound; and results of hERG electrophysiology could be used to evaluate a potential risk of QT interval prolongation of the compound. When a hERG semi-inhibitory concentration of a medicine exceeded about 30 times of a peak concentration thereof in blood, the concentration was in a relatively safe range (Redfernelt al, Cardiovascular Research, 58, 32-45 (2003)).

Experiment results were shown in Table 6.

TABLE 6

Inhibition Ratio of Tested Compound to hERG Current and IC50 Results:

| Compound | hERG current inhibition ratio % | | | | | n | IC50 |
|---|---|---|---|---|---|---|---|
| | 0.3 µM | 1 µM | 3 µM | 10 µM | 30 µM | | |
| 8a | 1.47% ± 1.33% | 5.53% ± 1.93% | 4.36% ± 2.80% | 11.24% ± 3.33% | 7.86% ± 2.61% | 3 | >30 µM |
| 8b | 3.56% ± 1.98% | 6.97% ± 2.74% | 11.32% ± 2.88% | 14.98% ± 1.09% | 21.88% ± 2.44% | 3 | >30 µM |

According to the standard above, the experimental results showed that the compounds 8a and 8b have no inhibitory effect on the hERG potassium channel, namely, the compounds 8a and 8b had no cardiotoxicity.

The invention claimed is:

1. A compound of formula I or a pharmaceutically acceptable salt thereof,

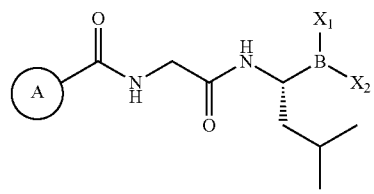

wherein $X_1$ and $X_2$ jointly form a circular portion derived from a boric acid esterifying agent by removing hydrogen atoms of two functional groups of said boric acid esterifying agent; the boric acid esterifying agent is selected from the group consisting of α-hydroxy acid, β-hydroxy acid, amino acid and $R_3$—NH—$R_4$; the $R_3$ and the $R_4$ are selected from —$(CH_2)_n$COOH, and n=0, 1, 2, 3, 4 or 5; and ring A is selected from the group consisting of:

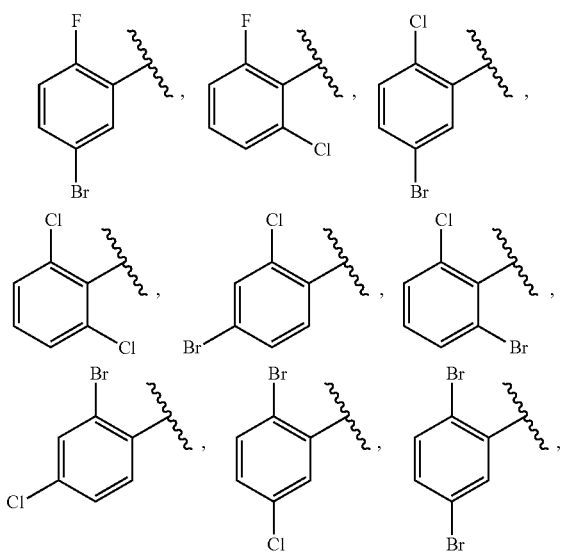

-continued

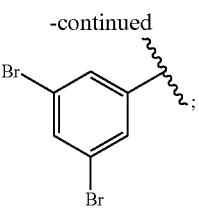

wherein, when the ring A is selected from the group consisting of

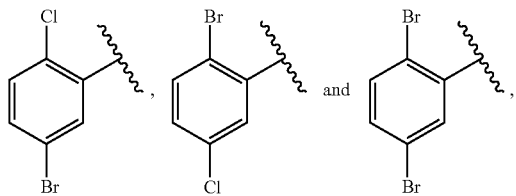

the α-hydroxy acid and the β-hydroxy acid do not comprise citric acid, malic acid and tartaric acid.

2. The compound or the pharmaceutically acceptable salt thereof according to claim 1, wherein the circular portion jointly formed by the $X_1$ and the $X_2$ by removing hydrogen atoms of two functional groups of the boric acid esterifying agent is a 5 to 12 membered ring.

3. The compound or the pharmaceutically acceptable salt thereof according to claim 2, wherein:

the boric acid esterifying agent is selected from the group consisting of salicylic acid, mandelic acid, lactic acid and iminodiacetic acid substituted by a substituent or unsubstituted; the substituent is selected from the group consisting of halogens, amino, C1-6 alkyls, C3-C8 cycloalkyls, C2-C6 carboxyalkyls and C1-6 hydroxyalkyls and a mixture thereof;

optionally, the phenyl in the salicylic acid or the mandelic acid substituted by a substituent or unsubstituted as the boric acid esterifying agent is hydrogenated or partially hydrogenated.

4. The compound or the pharmaceutically acceptable salt thereof according to claim 3, wherein when the ring A is

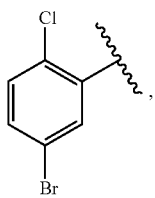

the boric acid esterifying agent is the salicylic acid, the mandelic acid or the lactic acid substituted by a substituent or unsubstituted, and the substituent is selected from the group consisting of halogens, amino, C1-6 alkyls, C2-C6 carboxyalkyls and C1-6 hydroxyalkyls and a mixture thereof.

5. The compound or the pharmaceutically acceptable salt thereof according to claim 3, wherein when the ring A is selected from the group consisting of

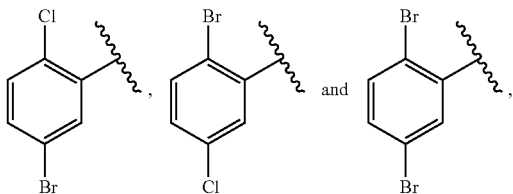

the boric acid esterifying agent is the salicylic acid, the R-mandelic acid or the L-lactic acid substituted by a substituent or unsubstituted; and the substituent is selected from the group consisting of halogens, amino, C1-6 alkyls, C2-C6 carboxyalkyls and C1-6 hydroxyalkyls and a mixture thereof; and optionally, the phenyl in the salicylic acid or the R-mandelic acid substituted by a substituent or unsubstituted as the boric acid esterifying agent is hydrogenated or partially hydrogenated.

6. The compound or the pharmaceutically acceptable salt thereof according to claim 5, wherein the compound is selected from the group consisting of:

compound 8a:

2-chloro-5-bromo-N-(2-{[(1R)-3-methyl-1-(4-oxo-4H-1,3,2-benzodioxaborolan-2-yl)butyl]amino}-2-oxoethyl)benzamide

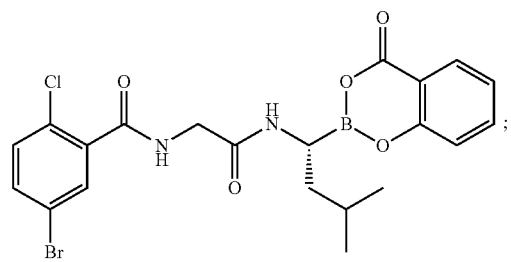

compound 8b:

2-chloro-5-bromo-N-[2-({(1R)-3-methyl-1-[(5R)-4-oxo-5-phenyl-1,3,2-dioxaborolan-2-yl]butyl}amino)-2-oxoethyl]benzamide

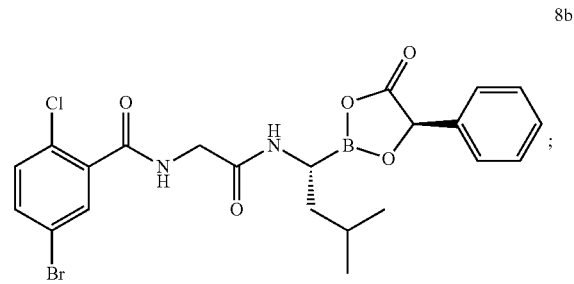 [SMILES: CC(C)C[C@H](NC(=O)CNC(=O)c1cc(Cl)ccc1Br)B1OC(=O)[C@@H](c2ccccc2)O1]

compound 8c:

2-chloro-5-bromo-N-[2-({(1R)-3-methyl-1-[(4S)-4-methyl-5-oxo-1,3,2-dioxaborolan-2-yl]butyl}amino)-2-oxoethyl]benzamide

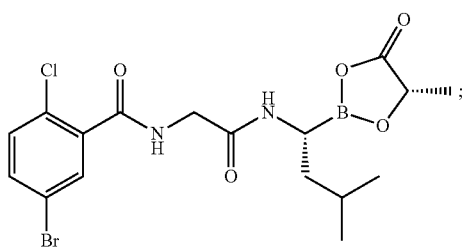

compound 8e:
2-bromo-5-bromo-N-(2-{[(1R)-3-methyl-1-(4-oxo-4H-1,3,2-benzodioxaborolan-2-yl)butyl]amino}-2-oxoethyl)benzamide

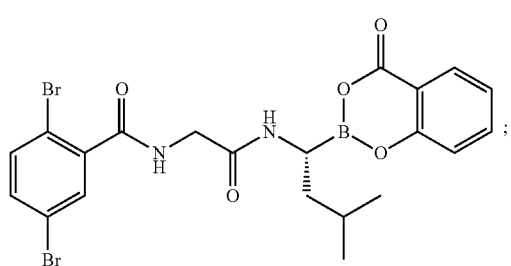

compound 8f:
2-bromo-5-bromo-N-[2-({(1R)-3-methyl-1-[(5R)-4-oxo-5-phenyl-1,3,2-dioxaborolan-2-yl]butyl}amino)-2-oxoethyl]benzamide

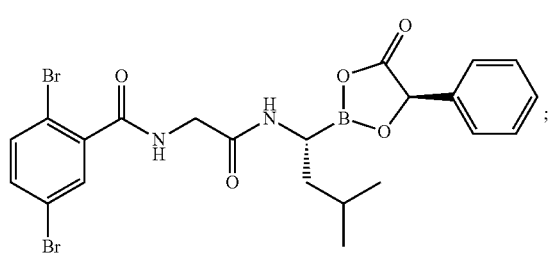

compound 8g:
2-bromo-5-bromo-N-[2-({(1R)-3-methyl-1-[(4S)-4-methyl-5-oxo-1,3,2-dioxaborolan-2-yl]butyl}amino)-2-oxoethyl]benzamide

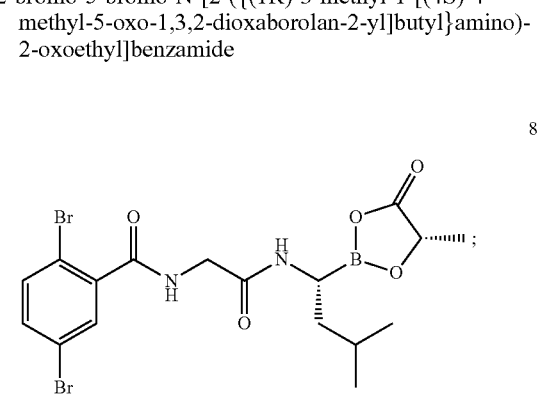

compound 8h:
2-bromo-5-chloro-N-(2-{[(1R)-3-methyl-1-(4-oxo-4H-1,3,2-benzodioxaborolan-2-yl)butyl]amino}-2-oxoethyl)benzamide

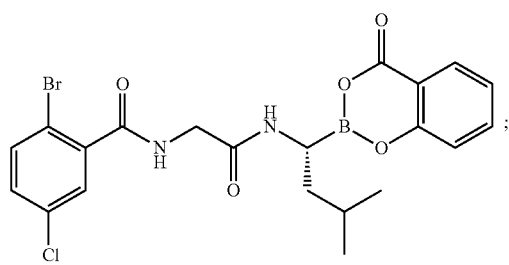

compound 8i:
2-bromo-5-chloro-N-[2-({(1R)-3-methyl-1-[(5R)-4-oxo-5-phenyl-1,3,2-dioxaborolan-2-yl]butyl}amino)-2-oxoethyl]benzamide

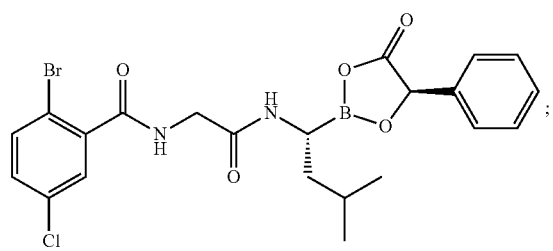

and compound 8j:
2-bromo-5-chloro-N-[2-({(1R)-3-methyl-1-[(4S)-4-methyl-5-oxo-1,3,2-dioxaborolan-2-yl]butyl}amino)-2-oxoethyl]benzamide

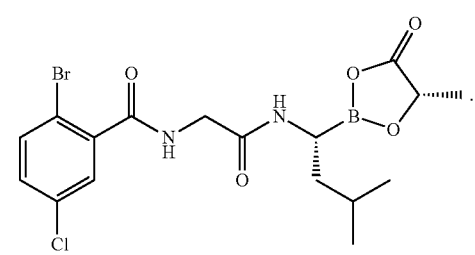

7. The compound or the pharmaceutically acceptable salt thereof according to claim 2, wherein the compound is selected from the group consisting of:

compound 8m:
2-chloro-5-bromo-N-[2-({(1R)-3-methyl-1-[(5S)-4-oxo-5-phenyl-1,3,2-dioxaborolan-2-yl]butyl}amino)-2-oxoethyl]benzamide

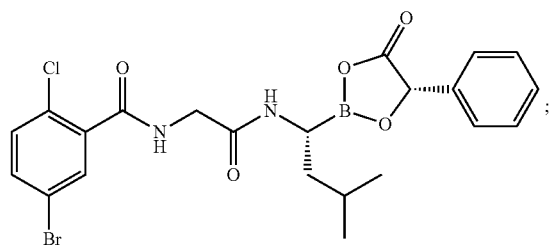

compound 8m and
compound 8n:
2-chloro-5-bromo-N-[2-({(1R)-3-methyl-1-[4-oxo-5-phenyl-1,3,2-dioxaborolan-2-yl]butyl}amino)-2-oxo-ethyl]benzamide

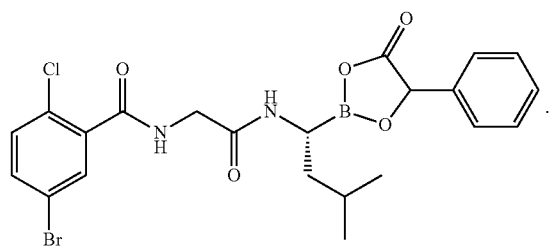

8. A preparation method for the compound according to claim 1, comprising the following steps of synthesis:

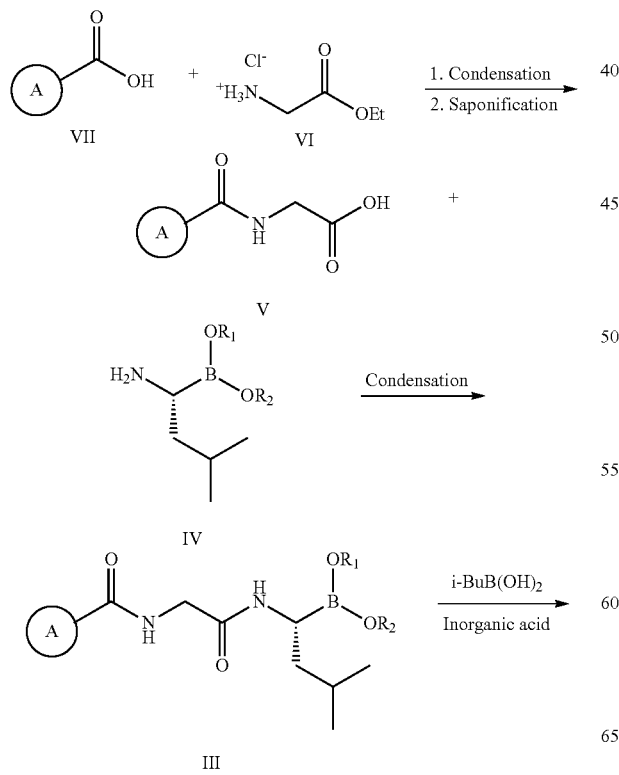

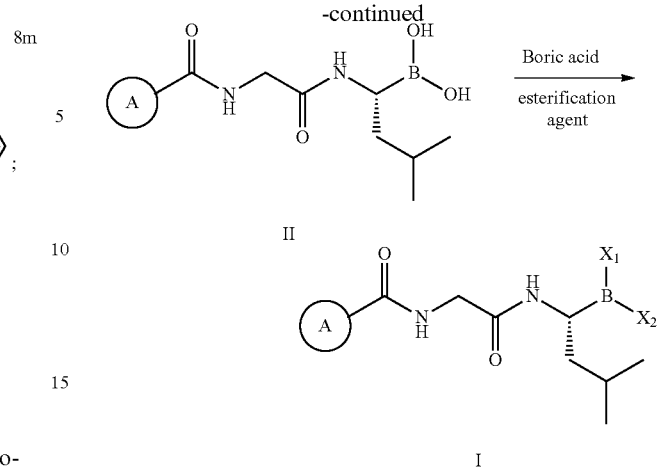

wherein, ring A, $X_1$ and $X_2$ are defined according to any one of claims 1 to 6;

a) using a compound of formula VII as an initial raw material, and obtaining a compound of formula V through condensation and saponification with glycine ethyl ester hydrochloride (formula VI);

b) condensing the compound of the formula V with a chiral α-aminoborate compound (formula IV) to obtain a compound of formula III;

c) hydrolyzing the compound of the formula III under a condition of inorganic acid to obtain a compound of formula II; and d) making the compound of the formula II react with the boric acid esterifying agent to obtain a compound of formula I;

wherein the $R_1$ and the $R_2$ in the formula IV are independently selected from a hydrogen atom, a C1-6 alkyl substituted by a substituent or unsubstituted, a C6-10 aryl substituted by a substituent or unsubstituted, a C7-18 arylalkyl substituted by a substituent or unsubstituted, a C3-15 cycloalkyl substituted by a substituent or unsubstituted, a C4-10 cycloalkyl alkyl substituted by a substituent or unsubstituted, 5-15 membered heteroaryl substituted by a substituent or unsubstituted, or a 6-21 membered heteroaryl alkyl substituted by a substituent or unsubstituted; or the $R_1$ and the $R_2$ together with a boron atom and an oxygen atom attached to the $R_1$ and the $R_2$ form a 5 to 10 membered carbonic ring substituted by a substituent or unsubstituted, the 5 to 10 membered carbonic ring substituted by a substituent or unsubstituted has 0 to 2 heteroatoms selected from nitrogen, oxygen and sulfur in addition to the boron atom and the two oxygen atoms linked thereto; and the substituent is selected from the group consisting of halogens, amino, C1-6 alkyls, C2-C6 carboxyalkyls and C1-6 hydroxyalkyls and a mixture thereof.

9. The preparation method according to claim 8, wherein:
a condensing agent used in the condensation reaction in the step a) is selected from the group consisting of TBTU, EDCI/HOBT and DCC/HOBT, and a reaction solvent used in the condensation reaction in the step a) is selected from the group consisting of dichloromethane, DMF and THF and a mixed solvent of two thereof; an alkali used in the saponification reaction in the step a) is LiOH, NaOH or KOH, and a reaction solvent is a mixed solvent of ethanol and water;

a condensing agent used in the condensation reaction in the step b) is selected from the group consisting of TBTU, EDCI/HOBT and DCC/HOBT; a reaction solvent used in the condensation reaction in the step b) is selected from the group consisting of dichloromethane, DMF and THF and a mixed solvent of two thereof; and $R_1$ and $R_2$ in the compound of the formula IV jointly form

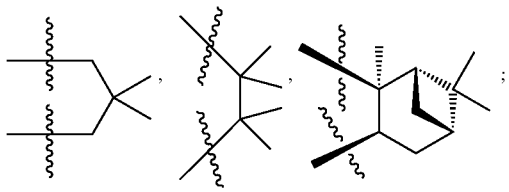

in the step c), the compound of the formula III is hydrolyzed by inorganic acid in methanol/n-hexane or methanol/n-heptane serving as a reaction solvent to generate the compound of the formula II; and the inorganic acid is selected from the group consisting of hydrochloric acid, sulfuric acid and nitric acid and a combination of more thereof; and in the step d), a reaction solvent is selected from the group consisting of ethyl acetate, THF, acetone, dichloromethane, n-hexane and heptane and a mixed solvent of two thereof; and a reaction temperature ranges from 0° C. to 100° C.

10. The preparation method according to claim 8, wherein the condensation reactions in the steps a) and b) are performed in presence of organic alkali.

11. A method of treating a cancer, said method comprising administering to a subject in need thereof a therapeutically effective amount of the compound of claim 1.

12. The compound or the pharmaceutically acceptable salt thereof according to claim 3, wherein:
the mandelic acid is R-mandelic acid or S-mandelic acid, and the lactic acid is L-lactic acid.

13. The compound or the pharmaceutically acceptable salt thereof according to claim 4, the boric acid esterifying agent is the salicylic acid or the R-mandelic acid.

14. The preparation method according to claim 9, wherein:
an alkali used in the saponification reaction in the step a) is NaOH;
a condensing agent used in the condensation reaction in the step b) is EDCI/HOBT;
a reaction solvent used in the condensation reaction in the step b) is dichloromethane;
in the step c), the inorganic acid is the hydrochloric acid; and
in the step d), a reaction solvent is ethyl acetate or a mixed solvent of ethyl acetate and n-hexane; and a reaction temperature ranges from 30° C. to 75° C.

15. The preparation method according to claim 10, wherein the organic alkali is DIPEA.

16. A method of inhibiting proteasome, the method comprising administering to a subject in need thereof a therapeutically effective amount of the compound of claim 1.

* * * * *